(12) United States Patent
Mayer et al.

(10) Patent No.: US 6,630,295 B2
(45) Date of Patent: Oct. 7, 2003

(54) HIGH THROUGHPUT ASSAY FOR MONITORING POLYCATION OR POLYANION MOLECULAR WEIGHT, DEGRADATION OR SYNTHESIS

(75) Inventors: Raphael Mayer, Kfar Bilu (IL); Simha Shemesh, Ramla (IL); Maty Ayal-Hershkovitz, Herzlia (IL)

(73) Assignee: Insight Strategy & Marketing Ltd., Rehovot (IL)

( * ) Notice: Subject to any disclaimer, the term of this patent is extended or adjusted under 35 U.S.C. 154(b) by 0 days.

(21) Appl. No.: 09/753,692

(22) Filed: Jan. 4, 2001

(65) Prior Publication Data

US 2002/0115071 A1 Aug. 22, 2002

(51) Int. Cl.[7] .................................................. C12Q 1/00
(52) U.S. Cl. ........................................................... 435/4
(58) Field of Search .......................... 435/4, 6; 436/172

(56) References Cited

U.S. PATENT DOCUMENTS

| | | | |
|---|---|---|---|
| 5,573,907 A | * 11/1996 | Carrino et al. | 435/6 |
| 6,190,875 B1 | * 2/2001 | Ben-Artzi et al. | 435/18 |
| 6,242,238 B1 | * 6/2001 | Freeman et al. | 435/200 |
| 6,329,142 B2 | * 12/2001 | Tsuruoka et al. | 435/6 |

OTHER PUBLICATIONS

Koszegi et al. Fluorexcence polarization o fantigen determinant peptides of human fibrinogen. Acta Biochim. et Biophys. Acad. Sci. Hung. vol. 19(3–4): 169–175, 1984.*
Gigli et al. A comparative study of low–density lipoprotein interaction with glycosaminoglycans Biochimica et Biophysica Acta vol. 1167:211–217, 1993.*
Clarke et al. Teh effect of teh chain length of heparin on its interaction with lipoprotein lipase. Bioch. Biophys. ACTA vol. 747:130–137, 1983.*

* cited by examiner

*Primary Examiner*—Remy Yucel
*Assistant Examiner*—William Sandals
(74) *Attorney, Agent, or Firm*—G. E. Ehrlich Ltd.

(57) ABSTRACT

A method of testing an agent for its potential at modulating induction of a molecular weight change of a first polyion is disclosed. The method is effected by (a) subjecting the first polyion to conditions under-which the first polyion undergoing the molecular weight change in a presence, in an absence or under several different concentrations of the agent; (b) interacting the first polyion with a second polyion having an opposite charge, the second polyion being fluorescently labeled; (c) providing reaction conditions so as to allow molecular weight discriminative interaction between the first polyion and the second polyion; and (d) employing a fluorescence polarization assay for determining a modulating effect of the agent on the induction of the molecular weight change of the first polyion.

24 Claims, 3 Drawing Sheets

HIGH THROUGHPUT ASSAY FOR MONITORING POLYCATION OR POLYANION MOLECULAR WEIGHT, DEGRADATION OR SYNTHESIS

FIELD AND BACKGROUND OF THE INVENTION

The present invention relates to a novel high throughput assay for monitoring polyion (polycation or polyanion) degradation or polymerization and for determining a molecular weight of a polyion. More particularly, the present invention relates to a high throughput assay for monitoring the activity of enzymes which either degrade or synthesize polyions and for screening for potential modulators (inhibitors or activators) of such enzymes, however, physical and chemical degradation/polymerization of polyions and modulators thereof can also be monitored by the method of the present invention. Most, particularly, the present invention relates to a high throughput assay for monitoring the catalytic activity of glycosaminoglycans (GAGs) degrading enzymes and for screening of modulators, especially inhibitors, thereof.

Proteoglycans (PGs):

Proteoglycans (previously named mucopolysaccharides) are remarkably complex molecules and are found in every tissue of the body. They are associated with each other and also with other major structural components, such as collagen and elastin. Some PGs interact with certain adhesive proteins, such as fibronectin and laminin.

Glycosaminoglycans (GAGs):

Glycosaminoglycans (GAGs) proteoglycans are polyanions and hence bind polycations and cations, such as $Na^+$ and $K^+$. This latter ability attracts water by osmotic pressure into the extracellular matrix and contributes to its turgor. GAGs also gel at relatively low concentrations. The long extended nature of the polysaccharide chains of GAGs and their ability to gel, allow relatively free diffusion of small molecules, but restrict the passage of large macromolecules. Because of their extended structures and the huge macromolecular aggregates they often form, they occupy a large volume of the extracellular matrix relative to proteins. Murry R K and Keeley F W; Harper's Biochemistry, 24th Ed. Ch. 57. pp. 667–85.

Heparan sulfate (HS) proteoglycans:

Heparan sulfate (HS) proteoglycans are acidic polysaccharide-protein conjugates associated with cell membranes and extracellular matrices. They bind avidly to a variety of biologic effector molecules, including extracellular matrix components, growth factor, growth factor binding proteins, cytokines, cell adhesion molecules, proteins of lipid metabolism, degradative enzymes, and protease inhibitors. Owing to these interactions, heparan sulfate proteoglycans play a dynamic role in biology, in fact most functions of the proteoglycans are attributable to the heparan sulfate chains, contributing to cell-cell interactions and cell growth and differentiation in a number of systems. It maintains tissue integrity and endothelial cell function. It serves as an adhesion molecule and presents adhesion-inducing cytokines (especially chemokines), facilitating localization and activation of leukocytes. The adhesive effect of heparan sulfate-bound chemokines can be abrogated by exposing the extracellular matrices to heparanase before or after the addition of chemokines. Heparan sulfate modulates the activation and the action of enzymes secreted by inflammatory cells. The function of heparan sulfate changes during the course of the immune response are due to changes in the metabolism of heparan sulfate and to the differential expression of and competition between heparan sulfate-binding molecules. Selvan R S et al.; Ann. NY Acad. Sci. 1996; 797:127–139.

Other PGs and GAGs, such as hyaluronic acid, chondroitin sulfates, keratan sulfates I, II, dermatan sulfate and heparin have also important physiological functions.

GAG degrading enzymes:

Degradation of GAGs is carried out by a battery of lysosomal hydrolases. These include certain endoglycosidases, such as, but not limited to, mammal heparanase (U.S. Pat. No. 5,968,822 for recombinant and WO91/02977 for native human heparanase) and connective tissue activating peptide III (CTAP, WO95/04158 for native and U.S. Pat. No. 4,897,348 for recombinant CTAP) which degrade heparan sulfate and to a lesser extent heparin; heparinase I, II and III (U.S. Pat No. 5,389,539 for the native form and WO95/34635 A1, U.S. Pat. No. 5,714,376 and U.S. Pat. No. 5,681,733 for the recombinant form), e.g., from *Flavobacterium heparinum* and Bacillus sp., which cleave heparin-like molecules; heparitinase T-I, T-II, T-III and T-VI from *Bacillus circulans* (U.S. Pat. No. 5,405,759, JO 4278087 and JP04-278087); β-glucoronidase; chondroitinase ABC (EC 4.2.2.4) from *Proteus vulgaris,* AC (EC 4.2.2.5) from *Arthrobacter aurescens* or *Flavobacterium heparinum,* B and C (EC 4.2.2) from *Flavobacterium heparinum* which degrade chondroitin sulfate; hyaluronidase from sheep or bovine testes which degrade hyaluronidase and chondroitin sulfate; various exoglycosidases (e.g., β-glucoronidase EC 3.2.1.31) from bovine liver, mollusks and various bacteria; and sulfatases (e.g., iduronate sulfatase) EC 3.1.6.1 from limpets (*Patella vulgaris*), *Aerobacter aerogens, Abalone entrails* and *Helix pomatia,* generally acting in sequence to degrade the various GAGs.

Heparanase:

One important enzyme involved in the catabolism of certain GAGs is heparanase. It is an endo-β-glucoronidase that cleaves heparan sulfate at specific interchain sites. Interaction of T and B lymphocytes, platelets, granulocytes, macrophages and mast cells with the subendothelial extracellular matrix (ECM) is associated with degradation of heparan sulfate by heparanase activity. The enzyme is released from intracellular compartments (e.g., lysosomes or specific granules) in response to various activation signals (e.g., thrombin, calcium ionophore, immune complexes, antigens and mitogens), suggesting its regulated involvement in inflammation and cellular immunity. Vlodavsky I et al.; Invasion Metas. 1992; 12(2):112–27.

Cloning and expression of the heparanase gene:

A purified fraction of heparanase isolated from human hepatoma cells was subjected to tryptic digestion. Peptides were separated by high pressure liquid chromatography and micro sequenced. The sequence of one of the peptides was used to screen data bases for homology to the corresponding back translated DNA sequence. This procedure led to the identification of a clone containing an insert of 1020 base pairs (bp) which included an open reading frame of 963 bp followed by 27 bp of 3' untranslated region and a poly A tail. The new gene was designated hpa. Cloning of the missing 5' end of hpa was performed by PCR amplification of DNA from placenta cDNA composite. The entire heparanase cDNA was designated phpa. The joined cDNA fragment contained an open reading frame which encodes a polypeptide of 543 amino acids with a calculated molecular weight of 61,192 daltons. Cloning an extended 5' sequence was enabled from the human SK-hep1 cell line by PCR amplification using the Marathon RACE system. The 5' extended sequence of the SK-hep1 hpa cDNA was assembled with the sequence of the hpa cDNA isolated from human placenta. The assembled sequence contained an open reading frame which encodes a polypeptide of 592 amino acids with a calculated molecular weight of 66,407 daltons. The cloning procedures are described in length in U.S. Pat. No. 5,968,822, PCT Application No. U.S. Ser. No. 98/17954 and U.S. patent application Ser. Nos. 09/109,386 now abandoned and 09/258,892 now abandoned.

The ability of the hpa gene product to catalyze degradation of heparan sulfate (HS) in vitro was examined by expressing the entire open reading frame of hpa in High five and Sf21 insect cells, and the mammalian human 293 embryonic kidney cell line expression systems. Extracts of infected cells were assayed for heparanase catalytic activity. For this purpose, cell lysates were incubated with sulfate labeled, ECM-derived HSPG (peak I), followed by gel filtration analysis (Sepharose 6B) of the reaction mixture. While the substrate alone consisted of high molecular weight material, incubation of the HSPG substrate with lysates of cells infected with hpa containing virus resulted in a complete conversion of the high molecular weight substrate into low molecular weight labeled heparan sulfate degradation fragments (see, for example, U.S. patent application Ser. No. 09/260,038 now U.S. Pat. No. 6,348,344).

In subsequent experiments, the labeled HSPG substrate was incubated with the culture medium of infected High Five and Sf21 cells. Heparanase catalytic activity, reflected by the conversion of the high molecular weight HSPG substrate into low molecular weight HS degradation fragments, was found in the culture medium of cells infected with the pFhpa virus, but not the control pF1 virus.

Altogether, these results indicate that the heparanase enzyme is expressed in an active form by cells infected with Baculovirus or mammalian expression vectors containing the newly identified human hpa gene.

In other experiments, it was demonstrated that the heparanase enzyme expressed by cells infected with the pFhpa virus is capable of degrading HS complexed to other macromolecular constituents (e.g., fibronectin, laminin, collagen) present in a naturally produced intact ECM (Ser. No. 09/260,038 now U.S. Pat. No. 6,348,344), in a manner similar to that reported for highly metastatic tumor cells or activated cells of the immune system (Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992) Expression of heparanase by platelets and circulating cells of the immune system: Possible involvement in diapedesis and extravasation. Invasion & Metastasis, 12, 112–127; Vlodavsky, I., Mohsen, M., Lider, O., Ishai-Michaeli, R., Ekre, H. -P., Svahn, C. M., Vigoda, M., and Peretz, T. (1995). Inhibition of tumor metastasis by heparanase inhibiting species of heparin. Invasion & Metastasis, 14: 290–302).

Purification of the recombinant heparanase enzyme:

Sf21 insect cells were infected with pFhpa virus and the culture medium was applied onto a heparin-Sepharose column. Fractions were eluted with a salt gradient (0.35–2.0 M NaCl) and tested for heparanase catalytic activity and protein profile (SDS/PAGE followed by silver staining). Heparanase catalytic activity correlated with the appearance of a about 63 kDa protein band in fractions 19–24, consistent with the expected molecular weight of the hpa gene product. Active fractions eluted from heparin-Sepharose were pooled, concentrated and applied onto a Superdex 75 FPLC gel filtration column. Aliquots of each fraction were tested for heparanase catalytic activity and protein profile. A correlation was found between the appearance of a major protein (approximate molecular weight of 63 kDa) in fractions 4–7 and heparanase catalytic activity. This protein was not present in medium conditioned by control non-infected Sf21 cells subjected to the same purification protocol. Recently, an additional purification protocol was applied, using a single step chromatography with source-S ion exchange column. This purification resulted in a purified protein to a degree of 90%. Further details concerning these purification procedures are disclosed in U.S. patent application Ser. Nos. 09/260,038 now U.S. Pat. No. 6,348,344 and 09/071,618 now abandoned, both are incorporated by reference as if fully set forth herein.

Involvement of heparanase in tumor cell invasion and metastasis:

Circulating tumor cells arrested in the capillary beds of different organs must invade the endothelial cell lining and degrade its underlying basement membrane (BM) in order to escape into the extravascular tissue(s) where they establish metastasis (Liotta, L. A., Rao, C. N., and Barsky, S. H. (1983). Tumor invasion and the extracellular matrix. Lab. Invest., 49, 639–649). Several cellular enzymes (e.g., collagenase IV, plasminogen activator, cathepsin B, elastase) are thought to be involved in degradation of the BM (Liotta, L. A., Rao, C. N., and Barsky, S. H. (1983). Tumor invasion and the extracellular matrix. Lab. Invest., 49, 639–649). Among these enzymes is an endo-β-D-glucuronidase (heparanase) that cleaves HS at specific intrachain sites (Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992). Expression of heparanase by platelets and circulating cells of the immune system: Possible involvement in diapedesis and extravasation. Invasion & Metastasis, 12, 112–127; Nakajima, M., Irimura, T., and Nicolson, G. L. (1988). Heparanase and tumor metastasis. J. Cell. Biochem., 36, 157–167; Vlodavsky, I., Fuks, Z., Bar-Ner, M., Ariav, Y., and Schirrmacher, V. (1983). Lymphoma cell mediated degradation of sulfated proteoglycans in the subendothelial extracellular matrix: Relationship to tumor cell metastasis. Cancer Res., 43, 2704–2711; Vlodavsky, I., Ishai-Michaeli, R., Bar-Ner, M., Fridman, R., Horowitz, A. T., Fuks, Z. and Biran, S. Involvement of heparanase in tumor metastasis and angiogenesis. Is. J. Med. 24:464–470, 1988). Expression of a HS degrading heparanase was found to correlate with the metastatic potential at mouse lymphoma (Vlodavsky, I., Fuks, Z., Bar-Ner, M., Ariav, Y., and Schirrmacher, V. (1983). Lymphoma cell mediated degradation of sulfated proteoglycans in the subendothelial extracellular matrix: Relationship to tumor cell metastasis. Cancer Res., 43, 2704–2711), fibrosarcoma and melanoma (Nakajima, M., Irimura, T., and Nicolson, G. L. (1988). Heparanase and tumor metastasis. J. Cell. Biochem., 36, 157–167) cells. The same is true for human breast, bladder and prostate carcinoma cells (see U.S. patent application Ser. No. 09/109,386 now abandoned, which is incorporated by reference as if fully set forth herein). Moreover, elevated levels of heparanase were detected in sera (Nakajima, M., Irimura, T., and Nicolson, G. L. (1988). Heparanase and tumor metastasis. J. Cell. Biochem., 36, 157–167) and urine (U.S. patent application Ser. No. 09/109,386 now abandoned) of metastatic tumor bearing animals and cancer patients and in tumor biopsies (Vlodavsky, I., Ishai-Michaeli, R., Bar-Ner, M., Fridman, R., Horowitz, A. T., Fuks, Z. and Biran, S. Involvement of heparanase in tumor metastasis and angiogenesis. Is. J. Med. 24:464–470, 1988). Treatment of experimental animals with heparanase alternative substrates and inhibitor (e.g., non-anticoagulant species of low molecular weight heparin, laminarin sulfate) markedly reduced (>90%) the incidence of lung metastases induced by B16 melanoma, Lewis lung carcinoma and mammary adenocarcinoma cells (Vlodavsky, I., Mohsen, M., Lider, O., Ishai-Michaeli, R., Ekre, H. -P., Svahn, C. M., Vigoda, M., and Peretz, T. (1995). Inhibition of tumor metastasis by heparanase inhibiting species of heparin. Invasion & Metastasis, 14: 290–302; Nakajima, M., Irimura, T., and Nicolson, G. L. (1988). Heparanase and tumor metastasis. J. Cell. Biochem., 36, 157–167; Parish, C. R., Coombe, D. R., Jakobsen, K. B., and Underwood, P. A. (1987). Evidence that sulfated polysaccharides inhibit tumor metastasis by blocking tumor cell-derived heparanase. Int. J. Cancer, 40, 511–517), indicating that heparanase inhibitors may be applied to inhibit tumor cell invasion and metastasis.

The studies on the control of tumor progression by its local environment, focus on the interaction of cells with the extracellular matrix (ECM) produced by cultured corneal and vascular endothelial cells (EC) (Vlodavsky, I., Liu, G. M., and Gospodarowicz, D. (1980). Morphological appearance, growth behavior and migratory activity of human tumor cells maintained on extracellular matrix vs. plastic. Cell, 19, 607–616; Vlodavsky, I., Bar-Shavit, R., Ishai-Michaeli, R., Bashkin, P., and Fuks, Z. (1991). Extracellular sequestration and release of fibroblast growth factor: a regulatory mechanism? Trends Biochem. Sci., 16, 268–271). This ECM closely resembles the subendothelium in vivo in its morphological appearance and molecular composition. It contains collagens (mostly type III and IV, with smaller amounts of types I and V), proteoglycans (mostly heparan sulfate- and dermatan sulfate- proteoglycans, with smaller amounts of chondroitin sulfate proteoglycans), laminin, fibronectin, entactin and elastin (Parish, C. R., Coombe, D. R., Jakobsen, K. B., and Underwood, P. A. (1987). Evidence that sulfated polysaccharides inhibit tumor metastasis by blocking tumor cell-derived heparanase. Int. J. Cancer, 40, 511–517; Vlodavsky, I., Liu, G. M., and Gospodarowicz, D. (1980). Morphological appearance, growth behavior and migratory activity of human tumor cells maintained on extracellular matrix vs. plastic. Cell, 19, 607–616). The ability of cells to degrade HS in the ECM was studied by allowing cells to interact with a metabolically sulfate labeled ECM, followed by gel filtration (Sepharose 6B) analysis of degradation products released into the culture medium (Vlodavsky, I., Fuks, Z., Bar-Ner, M., Ariav, Y., and Schirrmacher, V. (1983). Lymphoma cell mediated degradation of sulfated proteoglycans in the subendothelial extracellular matrix: Relationship to tumor cell metastasis. Cancer Res., 43, 2704–2711). While intact HSPG are eluted next to the void volume of the column (Kav<0.2, Mr of about $0.5 \times 10^6$), labeled degradation fragments of HS side chains are eluted more toward the Vt of the column (0.5<kav<0.8, Mr of about $5-7 \times 10^3$) (Vlodavsky, I., Fuks, Z., Bar-Ner, M., Ariav, Y., and Schirrmacher, V. (1983). Lymphoma cell mediated degradation of sulfated proteoglycans in the subendothelial extracellular matrix: Relationship to tumor cell metastasis. Cancer Res., 43, 2704–2711). Compounds which efficiently inhibit the ability of heparanase to degrade the above-described naturally produced basement membrane-like substrate, were also found to inhibit experimental metastasis in mice and rats (Vlodavsky, I., Mohsen, M., Lider, O., Ishai-Michaeli, R., Ekre, H. -P., Svahn, C. M., Vigoda, M., and Peretz, T. (1995). Inhibition of tumor metastasis by heparanase inhibiting species of heparin. Invasion & Metastasis, 14: 290–302; Nakajima, M., Irimura, T., and Nicolson, G. L. (1988). Heparanase and tumor metastasis. J. Cell. Biochem., 36, 157–167; Parish, C. R., Coombe, D. R., Jakobsen, K. B., and Underwood, P. A. (1987). Evidence that sulfated polysaccharides inhibit tumor metastasis by blocking tumor cell-derived heparanase. Int. J. Cancer, 40, 511–517; Coombe D R, Parish C R, Ramshaw I A, Snowden J M: Analysis of the inhibition of tumor metastasis by sulfated polysaccharides. Int J Cancer 1987; 39:82–8). A reliable in vitro screening system for heparanase inhibiting compounds may hence be applied to identify and develop potent anti-metastatic drugs.

Possible involvement of heparanase in tumor angiogenesis:

It was previously demonstrated that heparanase may not only function in cell migration and invasion, but may also elicit an indirect neovascular response (Vlodavsky, I., Bar-Shavit, R., Ishai-Michaeli, R., Bashkin, P., and Fuks, Z. (1991). Extracellular sequestration and release of fibroblast growth factor: a regulatory mechanism? Trends Biochem. Sci., 16, 268–271). The results suggest that the ECM HSPGs provide a natural storage depot for βFGF and possibly other heparin-binding growth promoting factors. Heparanase mediated release of active βFGF from its storage within ECM may therefore provide a novel mechanism for induction of neovascularization in normal and pathological situations (Vlodavsky, I., Bar-Shavit, R., Korner, G., and Fuks, Z. (1993). Extracellular matrix-bound growth factors, enzymes and plasma proteins. In Basement membranes: Cellular and molecular aspects (eds. D. H. Rohrbach and R. Timpl), pp 327–343. Academic press Inc., Orlando, Fla.; Thunberg L, Backstrom G, Grundberg H, Risenfield J, Lindahl U: Themolecular size of the antithrombin-binding sequence in heparin. FEBS Lett 1980; 117:203–206).

Expression of heparanase by cells of the immune system:

Heparanase catalytic activity correlates with the ability of activated cells of the immune system to leave the circulation and elicit both inflammatory and autoimmune responses. Interaction of platelets, granulocytes, T and B lymphocytes, macrophages and mast cells with the subendothelial ECM is associated with degradation of heparan sulfate (HS) by heparanase catalytic activity (Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992). Expression of heparanase by platelets and circulating cells of the immune system: Possible involvement in diapedesis and extravasation. Invasion & Metastasis, 12, 112–127). The enzyme is released from intracellular compartments (e.g., lysosomes, specific granules) in response to various activation signals (e.g., thrombin, calcium ionophore, immune complexes, antigens, mitogens), suggesting its regulated involvement and presence in inflammatory sites and autoimmune lesions. Heparan sulfate degrading enzymes released by platelets and macrophages are likely to be present in atherosclerotic lesions (Campbell, K. H., Rennick, R. E., Kalevich, S. G., and Campbell, G. R. (1992) Exp. Cell Res. 200, 156–167). Treatment of experimental animals with heparanase alternative substrates (e.g., non-anticoagulant species of low molecular weight heparin) markedly reduced the incidence of experimental autoimmune encephalomyelitis (EAE), adjuvant arthritis and graft rejection (Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992). Expression of heparanase by platelets and circulating cells of the immune system: Possible involvement in diapedesis and extravasation. Invasion & Metastasis, 12, 112–127; Lider, O., Baharav, E., Mekori, Y., Miller, T., Naparstek, Y., Vlodavsky, I. and Cohen, I. R. Suppression of experimental autoimmune diseases and prolongation of allograft survival by treatment of animals with heparinoid inhibitors of T lymphocyte heparanase. J. Clin. Invest. 83:752–756, 1989) in experimental animals, indicating that heparanase inhibitors may be applied to inhibit autoimmune and inflammatory diseases (Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992). Expression of heparanase by platelets and circulating cells of the immune system: Possible involvement in diapedesis and extravasation. Invasion & Metastasis, 12, 112–127; Lider, O., Baharav, E., Mekori, Y., Miller, T., Naparstek, Y., Vlodavsky, I. and Cohen, I. R. Suppression of experimental autoimmune diseases and prolongation of allograft survival by treatment of animals with heparinoid inhibitors of T lymphocyte heparanase. J. Clin. Invest. 83:752–756, 1989). A reliable in vitro screening system for heparanase inhibiting compounds may hence be applied to identify and develop non-toxic anti-inflammatory drugs for the treatment of multiple sclerosis and other inflammatory diseases.

Recombinant heparanase for screening purposes:

Research aimed at identifying and developing inhibitors of heparanase catalytic activity has been handicapped by the lack of a consistent and constant source of a purified and highly active heparanase enzyme and of a reliable screening system. The recent cloning, expression and purification of the human heparanase-encoding gene offer, for the first time, a most appropriate and reliable source of active recombinant enzyme for screening of anti-heparanase antibodies and small compounds which may inhibit the enzyme and hence be applied to identify and develop drugs that may inhibit tumor metastasis, autoimmune and inflammatory diseases.

Screening for specific inhibitors using a combinatorial library:

A new approach aimed at rational drug discovery was recently developed for screening for specific biological activities. According to the new approach, a large library of chemically diversed molecules are screened for the desired biological activity. The new approach has become an effective and hence important tool for discovery of new drugs. The new approach is based on "combinatorial" synthesis of a diverse set of molecules in which several components predicted to be associated with the desired biological activity are systematically varied. The advantage of a combinatorial library over the alternative use of natural extracts for screening for desired biologically active compounds is that all the components comprising the library are known in advance (Farndale R. W., Sayers C. A., Barrett A. J. A Direct spectrophotometric microassay for sulfated glycosaminoglycans in cartilage cultures. Connective Tissue Res. 1990; 24: 267–275).

In combinatorial screening, the number of hits discovered is proportional to the number of molecules tested. This is true even when knowledge concerning the target is unavailable. The large number of compounds, which may reach thousands of compounds tested per day, can only be screened, provided that a suitable assay involving a high throughput screening technique, in which laboratory automation and robotics may be applied, exists.

Prior art heparanase catalytic activity assays:

Several methods for determining heparanase catalytic activity have been developed throughout the years. Many of the different methods are based on radiolabeling of a substrate (either in vitro or metabolically, as described above) and analysis of its degradation products released due to heparanase catalytic activity. These prior art methods suffer several disadvantages and limitations as follows.

First, the measurement of catalytic activity is qualitative and not quantitative. This is due to the following reasons (i) the radioactive labeling is not spread evenly along the substrate chain, therefore, radioactivity may not correlate precisely with activity; (ii) since heparanase substrates are long substrate chains, a released product can be, in fact, a substrate of heparanase, however while executing any of the prior art methods, cleavage events of released products are not monitorable. Moreover, multiple cleavage events of small portions of the substrate chain are indistinguishable from fewer cleavage events, yet of longer substrate chains. Thus, not all, and in many cases, depending on the substrate chain length, not even most, of the cleavage events catalyzed by the enzyme are detectable, thereby affecting the linearity of the assay.

Second, these prior art methods are cumbersome, time-consuming and do not allow activity determination of a large number of samples simultaneously. In most cases, both preparation of the radiolabeled substrate and separation of the degradation products from the uncleaved substrate involve long and complex procedures and handling with radioactive material which calls strict safety procedures.

Third, these prior art methods for determining heparanase catalytic activity involve modification of the substrate by either iodination at glucosamine residues, or either O- or N-acetylation of the partially de-N-sulfated substrate. Such procedures may result in masking heparanase cleavage sites, or alternatively creating new heparanase sites.

These different prior art methods also have specific disadvantages specifically associated with each of which. Some methods involve biosynthetic radiolabeling of ECM associated HSPG and detection of HS chain degradation by gel filtration analysis of the radiolabeled material released from the labeled ECM (Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992). Expression of heparanase by platelets and circulating cells of the immune system: Possible involvement in diapedesis and extravasation. Invasion & Metastasis, 12, 112–127; Bartlett M. R., Underwood P. A., Parish C. R.: Comparative analysis of the ability of leukocytes, endothelial cells and platelets to degrade the subendothelial basement membrane: evidence for cytokine dependence and detection of a novel sulfatase. Immonol. Cell Biol. 1995; 73: 113–124). In these assays, detection of the products requires a synergistic activity of proteases and heparanase. Protease is required to expose HS chains to cleavage by heparanase.

Other methods involve immobilizing chemically or biosynthetically radiolabeled heparanase substrate chains (Nakajima M., Irimura T., Nicolson G. L: A solid phase substrate of heparanase: its application to assay of human melanoma for heparan sulfate degradative activity. Anal. Biochem. 1986; 157: 162–171; Oosta G. M., Favreau L. V., Beeler D. L. Rosenberg R. D: 1982. J. Biol. Chem. 257, 11249–11255; Sewell R F, Brenchley P E G, Mallick N P: Human mononuclear cells contain an endoglycosidase specific for heparan sulfate glycosaminoglycan demonstrated with the use of a specific solid-phase metabolically radio-labelled substrate. Biochem. J. 1989; 264: 777–783). The main disadvantage of these methods is that the immobilized substrate may be less accessible to the enzyme.

In the heparanase catalytic activity assay recently developed by Freeman and Parish (Freeman C, Parish C R: A rapid and quantitative assay for the detection of mammalian heparanase catalytic activity. Biochem J. 1997; 325: 229–237) the products are separated from the substrate by binding to chicken histidine-rich glycoprotein (cHRG) sepharose. In this method only the lowest molecular weight products that lose the ability to bind to cHRG sepharose are detectable, while other, longer, products bind to the column with the substrate and are therefore excluded.

The mechanism by which heparanase operates on its substrate is still unknown and it is possible that some chains may first be cleaved to longer chains and then further be degraded to smaller fragments, while other chains may be directly cleaved at the end of thereof to form small fragments. The method by Freeman and Parish, therefore, fails to detect all of the cleavage products and therefore, like all of the other prior art methods described above for assaying heparanase catalytic activity, it is qualitative rather than quantitative.

Most importantly, these heparanase activity assays are not at all adapted for automated high throughput screening.

Colorimetric heparanase assays:

PCT/US99/15643 teaches several qualitative and quantitative colorimetric assays for the detection of heparanase catalytic activity based on carbazole and dimethylmethylene blue and the detection of newly made reducing ends produced by each cleavage action of the enzyme. An inherent disadvantage to each one of these assays is that they are multiple steps assays, requiring filtration (size exclusion) steps and the like which render them inapplicable for real high throughput automated screening.

Fluorimetric heparanase assays:

Several fluorescent techniques have been developed to assay heparanase catalytic activity. These techniques are based on size exclusion separation of fluorescently labeled reaction products. For example, Toyoshima and Nakajima (Toyoshima M, Nakajima M. 1999. Human heparanase. Purification, characterization, cloning, and expression. *J. Biol. Chem.* 274(34):24153–60), have recently developed an assay based on high speed gel permeation chromatography of the degradation products of fluorescein isothiocyanate-labeled heparan sulfate. Partially desulfation of heparin and labeling of the resulting free amine with fluoresceinylthiocarbamoyl was previously described (Uchiyama H, Nagasawa K 1981 Preparation of biologically active fluorescent heparin composed of fluorescein-labeled species and its behavior to antithrombin III. *J Biochem* (*Tokyo*) Jan; 89(1):185–92). Reaction of 5-aminofluorescein with uronic acid residues of several glycosaminoglycuronans have yielded fluorescent glycosaminoglycuronan derivatives (Ogamo A, Matsuzaki K, Uchiyama H, Nagasawa K 1982. Preparation and properties of fluorescent glycosaminoglycuronans labeled with 5-aminofluorescein. *Carbohydr Res* July 1;105(1):69–85).

In a somewhat different approach, a fluorescently labeled solid phase substrate, which yields soluble labeled products upon hydrolysis, is detected following phase separation. Additional methods are labeling of either at least partially N-deacylated or N-desulfated glycosaminoglycan with (i) a substance and yielding detectable signals to produce labeled glycosaminoglycan; or, (ii) completely N-acylating the labeled glycosaminoglycan with acyl anhydride or acyl halide; or (iii) reductively aminating a reducing terminal end of said labeled glycosaminoglycan to produce labeled amine-terminal glycosaminoglycan; and (iv) coupling, through its terminal amine, the labeled amine-terminal glycosaminoglycan to an amino-reactive solid phase support to produce the solid phase substrate (U.S. Pat. Nos. 5,332,812 and 4,859,581).

Fluorescence polarization:

Fluorescence polarization was first described in 1926 (Perrin (1926) *J. Phys. Rad.* 1: 390–401) and has been a powerful tool in the study of molecular interactions. When fluorescent molecules are excited with plane polarized light, they emit light in the same polarized plane, provided that the molecule remains stationary throughout the excited state (e.g., 4 nanoseconds in the case of fluorescein). However, if the excited molecule rotates or tumbles out of the plane of polarized light during the excited state, then light is emitted in a different plane from that of the initial excitation. If vertically polarized light is used to excite a fluorophore, the emission light intensity can be monitored in both the original vertical plane and also the horizontal plane. The degree to which the emission intensity moves from the vertical to horizontal plane is related to the mobility of the fluorescently labeled molecule. If fluorescently labeled molecules are very large, they move very little during the excited state interval, and the emitted light remains highly polarized within the excitation plane. If the fluorescently labeled molecules are small, they rotate or tumble faster, and the emitted light is depolarized relative to the excitation plane.

Fluorescence polarization (P) is defined as:

$$P = \frac{Int_{II} - Int_I}{Int_{II} + Int_I}$$

where Int(parallel) is the intensity of the emission light parallel to the excitation light plane and Int(perpendicular) is the intensity of the emission light perpendicular to the excitation light plane. P, being a ratio of light intensities, is dimensionless and has a maximum value of 0.5 for fluorescein. The Beacon System expresses polarization in millipolarization units (1 polarization Unit=1000 mP Units).

Fluorescence polarization in heparin binding assays:

Heparin has affinity to many different proteins. At one extreme the interaction between heparin and several proteins is highly specific depending on particular unusual polysaccharide sequence. Jones et al. (Jones G R, Hashim R, Power D M 1986. A comparison of the strength of binding of antithrombin III, protamine and poly(L-lysine) to heparin samples of different anticoagulant activities. *Biochim Biophys Acta* August 6;883(1):69–76) have shown that heparin labeled with 5-isothiocyanatofluorescein, where the dye was mostly bound to unsulphated glucosamine residues, exhibited binding which was characteristic of heparin with a low affinity for antithrombin III. On the other hand, heparin is very acidic due to its heavy substitution with sulfate groups and will bind readily to basic areas of protein surfaces in a relatively nonspecific fashion. The simplest peptides that bind to heparin are basic homopolypeptides such as poly-lysine and poly-arginine. It has long been established that heparin induces the formation of alpha-helix in these peptides (Gelman R A, Blackwell J 1973. Heparin-polypeptide interactions in aqueous solution. *Arch. Biochem. Biophys.* 159(1):427–33).

Using circular dichroism analysis, Mulloy et al. (Mulloy B, Crane D T, Drake A F, Davies D B 1996. The interaction between heparin and poly-lysine: a circular dichroism and molecular modeling study. *Braz J Med Biol Res* June; 29(6):721–9) have found that heparin oligosaccharides as small as an octasaccharide can still promote alpha-helix in poly-(L-lysine); the hexa- and tetrasaccharides do not, but they do disturb to a lesser extent the dynamic conformation equilibrium associated with poly-L-lysine at pH 7.0 at 22 degrees C. In a comparison of the strength of binding of antithrombin III, protamine and poly(L-lysine) to heparin samples of different anticoagulant activities, Jones et al. (Jones G R, Hashim R, Power D M 1986. A comparison of the strength of binding of antithrombin III, protamine and poly(L-lysine) to heparin samples of different anticoagulant activities. *Biochim Biophys Acta* August 6;883(1):69–76) have shown that limiting concentrations, i.e., those concentrations of sodium chloride required to completely disrupt the complexes of heparin with antithrombin III, protamine and poly(L-lysine), can be determined using fluorescence polarization techniques. They have shown that, from the limiting salt concentration values, poly(L-lysine) always exhibited stronger binding to heparin of a particular anticoagulant potency (degree of sulphation) than did protamine. The binding strengths of both complexes decreased as the degree of sulphation of the heparin participating in the complex was reduced.

The prior art, however, fails to teach a fluorescence polarization based assay for monitoring polyion (polycation or polyanion) molecular weight and changes thereof due to degradation or polymerization.

There is thus a widely recognized need for, and it would be highly advantageous to have, a fluorescence polarization based assay for monitoring polyion (polycation or polyanion) degradation or polymerization, so as to provide a high throughput assay for monitoring the activity of enzymes which degrade or polymerize polyions and for screening for potential modulators (inhibitors or activators) of such enzymes and/or to monitor physical or chemical degradation or polymerization processes of polyions, and modulators thereof. There is also a need of a fluorescence polarization based assay for determining the molecular weight of a polyion of unknown molecular weight in a sample.

SUMMARY OF THE INVENTION

While reducing the present invention to practice, an assay that utilizes the ability of NaCl to induce dissociation between heparin (a polyanion) and poly-(L-lysine) (a polycation) was developed. It was experimentally found that different limiting concentrations were required to dissociate poly-(L-lysine) and heparin of different molecular weight. This information was used to develop a potent high throughput fluorescence polarization based assay that discriminates between heparin and heparin degradation products, which assay serves as an example of the many fluorescence polarization assays provided by the present invention as is further delineated hereinbelow, all of which are based on the ability of reaction conditions, such as ionic strength, pH, temperature and/or viscosity, to induce dissociation/association between interacting polyanions and polycations in a molecular weight dependent manner.

Thus, according to the present invention there is provided a method of determining a molecular weight (e.g., an absolute or averaged molecular weight) of a first polyion in a sample, the method comprising the steps of (a) interacting the first polyion with a second polyion having an opposite charge, the second polyion being fluorescently labeled; (b) providing reaction conditions so as to allow molecular weight discriminative interaction between the first polyion and the second polyion; and (c) employing a fluorescence polarization assay for determining the molecular weight of the first polyion. Such a determination can be made using a calibration curve employing to this end samples of the first polyion of a known molecular weight.

This basic method can be used, according to the teachings of the present invention, to monitor molecular weight changes of a variety of polyions, as follows.

Hence, according to one aspect of the present invention there is provided a method of monitoring a molecular weight change of a first polyion, the method comprising the steps of (a) subjecting the first polyion to conditions under-which the first polyion undergoing the molecular weight change; (b) interacting the first polyion with a second polyion having an opposite charge, the second polyion being fluorescently labeled; (c) providing reaction conditions so as to allow molecular weight discriminative interaction between the first polyion and the second polyion; and (d) employing a fluorescence polarization assay for monitoring the molecular weight change of the first polyion.

According to another aspect of the present invention there is provided a method of monitoring a molecular weight change of a polyanion, the method comprising the steps of (a) subjecting the polyanion to conditions under-which the polyanion undergoing the molecular weight change; (b) interacting the polyanion with a polycation, the polycation being fluorescently labeled; (c) providing reaction conditions so as to allow molecular weight discriminative interaction between the polyanion and the polycation; and (d) employing a fluorescence polarization assay for monitoring the molecular weight change of the polyanion.

According to still another aspect of the present invention there is provided a method of monitoring a molecular weight change of a polycation, the method comprising the steps of (a) subjecting the polycation to conditions under-which the polycation undergoing the molecular weight change; (b) interacting the polycation with a polyanion, the polyanion being fluorescently labeled; (c) providing reaction conditions so as to allow molecular weight discriminative interaction between the polycation and the polyanion; and (d) employing a fluorescence polarization assay for monitoring the molecular weight change of the polycation.

According to yet still another aspect of the present invention there is provided a method of monitoring degradation of a first polyion, the method comprising the steps of (a) subjecting the first polyion to degradation inducing conditions; (b) interacting the first polyion with a second polyion having an opposite charge, the second polyion being fluorescently labeled; (c) providing reaction conditions so as to allow molecular weight discriminative interaction between the first polyion and the second polyion; and (d) employing a fluorescence polarization assay for monitoring a molecular weight change of the first polyion.

According to yet another aspect of the present invention there is provided a method of monitoring degradation of a polyanion, the method comprising the steps of (a) subjecting the polyanion to degradation inducing conditions; (b) interacting the polyanion with a polycation, the polycation being fluorescently labeled; (c) providing reaction conditions so as to allow molecular weight discriminative interaction between the polyanion and the polycation; and (d) employing a fluorescence polarization assay for monitoring a molecular weight change of the polyanion.

According to still another aspect of the present invention there is provided a method of monitoring degradation of a polycation, the method comprising the steps of (a) subjecting the polycation to degradation inducing conditions; (b) interacting the polycation with a polyanion, the polyanion being fluorescently labeled; (c) providing reaction conditions so as to allow molecular weight discriminative interaction between the polycation and the polyanion; and (d) employing a fluorescence polarization assay for monitoring a molecular weight change of the polycation.

According to yet another aspect of the present invention there is provided a method of monitoring polymerization of a first polyion, the method comprising the steps of (a) subjecting the first polyion to polymerization inducing conditions; (b) interacting the first polyion with a second polyion having an opposite charge, the second polyion being fluorescently labeled; (c) providing reaction conditions so as to allow molecular weight discriminative interaction between the first polyion and the second polyion; and (d) employing a fluorescence polarization assay for monitoring a molecular weight change of the first polyion.

According to still another aspect of the present invention there is provided a method of monitoring polymerization of a polyanion, the method comprising the steps of (a) subjecting the polyanion to polymerization inducing conditions; (b) interacting the polyanion with a polycation, the polycation being fluorescently labeled; (c) providing reaction conditions so as to allow molecular weight discriminative interaction between the polyanion and the polycation; and (d) employing a fluorescence polarization assay for monitoring a molecular weight change of the polyanion.

According to yet another aspect of the present invention there is provided a method of monitoring polymerization of a polycation, the method comprising the steps of (a) subjecting the polycation to polymerization inducing conditions; (b) interacting the polycation with a polyanion, the polyanion being fluorescently labeled; (c) providing reaction conditions so as to allow molecular weight discriminative interaction between the polycation and the polyanion; and (d) employing a fluorescence polarization assay for monitoring a molecular weight change of the polycation.

According to still another aspect of the present invention there is provided a method of testing an agent for its potential at modulating induction of a molecular weight change of a first polyion, the method comprising the steps of (a) subjecting the first polyion to conditions under-which the first polyion undergoing the molecular weight change in a presence, in an absence or under several different concentrations of the agent; (b) interacting the first polyion with a second polyion having an opposite charge, the second polyion being fluorescently labeled; (c) providing reaction conditions so as to allow molecular weight discriminative interaction between the first polyion and the second polyion; and (d) employing a fluorescence polarization assay for determining a modulating effect of the agent on the induction of the molecular weight change of the first polyion.

According to yet another aspect of the present invention there is provided a method of testing an agent for its potential at modulating induction of a molecular weight change of a polyanion, the method comprising the steps of (a) subjecting the polyanion to conditions under-which the polyanion undergoing the molecular weight change in a presence, in an absence or under several different concentrations of the agent; (b) interacting the polyanion with a polycation, the polycation being fluorescently labeled; (c) providing reaction conditions so as to allow molecular weight discriminative interaction between the polyanion and the polycation; and (d) employing a fluorescence polarization assay for determining a modulating effect of the agent on the induction of the molecular weight change of the polyanion.

According to still another aspect of the present invention there is provided a method of testing an agent for its potential at modulating induction of a molecular weight change of a polycation, the method comprising the steps of (a) subjecting the polycation to conditions under-which the polycation undergoing the molecular weight change in a presence, in an absence or under several different concentrations of the agent; (b) interacting the polycation with a polyanion, the polyanion being fluorescently labeled; (c) providing reaction conditions so as to allow molecular weight discriminative interaction between the polycation and the polyanion; and (d) employing a fluorescence polarization assay for determining a modulating effect of the agent on the induction of the molecular weight change of the polycation.

According to another aspect of the present invention there is provided a method of testing an agent for its potential at modulating induction of degradation of a first polyion, the method comprising the steps of (a) subjecting the first polyion to degradation inducing conditions in a presence, in an absence or under several different concentrations of the agent; (b) interacting the first polyion with a second polyion having an opposite charge, the second polyion being fluorescently labeled; (c) providing reaction conditions so as to allow molecular weight discriminative interaction between the first polyion and the second polyion; and (d) employing a fluorescence polarization assay for determining a modulating effect of the agent on the induction of the molecular weight change of the first polyion.

According to yet another aspect of the present invention there is provided a method of testing an agent for its potential at modulating induction of degradation of a polyanion, the method comprising the steps of (a) subjecting the polyanion to degradation inducing conditions in a presence, in an absence or under several different concentrations of the agent; (b) interacting the polyanion with a polycation, the polycation being fluorescently labeled; (c) providing reaction conditions so as to allow molecular weight discriminative interaction between the polyanion and the polycation; and (d) employing a fluorescence polarization assay for determining a modulating effect of the agent on the induction of the molecular weight change of the polyanion.

According to still another aspect of the present invention there is provided a method of testing an agent for its potential at modulating induction of degradation of a polycation, the method comprising the steps of (a) subjecting the polycation to degradation inducing conditions in a presence, in an absence or under several different concentrations of the agent; (b) interacting the polycation with a polyanion, the polyanion being fluorescently labeled; (c) providing reaction conditions so as to allow molecular weight discriminative interaction between the polycation and the polyanion; and (d) employing a fluorescence polarization assay for determining a modulating effect of the agent on the induction of the molecular weight change of the polycation.

According to another aspect of the present invention there is provided a method of testing an agent for its potential at modulating induction of polymerization of a first polyion, the method comprising the steps of (a) subjecting the first polyion to polymerization inducing conditions in a presence, in an absence or under several different concentrations of the agent; (b) interacting the first polyion with a second polyion having an opposite charge, the second polyion being fluorescently labeled; (c) providing reaction conditions so as to allow molecular weight discriminative interaction between the first polyion and the second polyion; and (d) employing a fluorescence polarization assay for determining a modulating effect of the agent on the induction of the molecular weight change of the first polyion.

According to yet another aspect of the present invention there is provided a method of testing an agent for its potential at modulating induction of polymerization of a polyanion, the method comprising the steps of (a) subjecting the polyanion to polymerization inducing conditions in a presence, in an absence or under several different concentrations of the agent; (b) interacting the polyanion with a polycation, the polycation being fluorescently labeled; (c) providing reaction conditions so as to allow molecular weight discriminative interaction between the polyanion and the polycation; and (d) employing a fluorescence polarization assay for determining a modulating effect of the agent on the induction of the molecular weight change of the polyanion.

According to still another aspect of the present invention there is provided a method of testing an agent for its potential at modulating induction of polymerization of a polycation, the method comprising the steps of (a) subjecting the polycation to polymerization inducing conditions in a presence, in an absence or under several different concentrations of the agent; (b) interacting the polycation with a polyanion, the polyanion being fluorescently labeled; (c) providing reaction conditions so as to allow molecular weight discriminative interaction between the polycation and the polyanion; and (d) employing a fluorescence polarization assay for determining a modulating effect of the agent on the induction of the molecular weight change of the polycation.

According to another aspect of the present invention there is provided a method of testing an agent for its potential at inhibiting induction of a molecular weight change of a first polyion, the method comprising the steps of (a) subjecting the first polyion to conditions under-which the first polyion undergoing the molecular weight change in a presence, in an absence or under several different concentrations of the agent; (b) interacting the first polyion with a second polyion having an opposite charge, the second polyion being fluorescently labeled; (c) providing reaction conditions so as to allow molecular weight discriminative interaction between the first polyion and the second polyion; and (d) employing a fluorescence polarization assay for determining an inhibiting effect of the agent on the induction of the molecular weight change of the first polyion.

According to yet another aspect of the present invention there is provided a method of testing an agent for its potential at inhibiting induction of a molecular weight change of a polyanion, the method comprising the steps of (a) subjecting the polyanion to conditions under-which the polyanion undergoing the molecular weight change in a presence, in an absence or under several different concentrations of the agent; (b) interacting the polyanion with a polycation, the polycation being fluorescently labeled; (c) providing reaction conditions so as to allow molecular weight discriminative interaction between the polyanion and the polycation; and (d) employing a fluorescence polarization assay for determining an inhibiting effect of the agent on the induction of the molecular weight change of the polyanion.

According to still another aspect of the present invention there is provided a method of testing an agent for its potential at inhibiting induction of a molecular weight change of a polycation, the method comprising the steps of (a) subjecting the polycation to conditions under-which the polycation undergoing the molecular weight change in a presence, in an absence or under several different concentrations of the agent; (b) interacting the polycation with a polyanion, the polyanion being fluorescently labeled; (c) providing reaction conditions so as to allow molecular weight discriminative interaction between the polycation and the polyanion; and (d) employing a fluorescence polarization assay for determining an inhibiting effect of the agent on the induction of the molecular weight change of the polycation.

According to another aspect of the present invention there is provided a method of testing an agent for its potential at inhibiting induction of degradation of a first polyion, the method comprising the steps of (a) subjecting the first polyion to degradation inducing conditions in a presence, in an absence or under several different concentrations of the agent; (b) interacting the first polyion with a second polyion having an opposite charge, the second polyion being fluorescently labeled; (c) providing reaction conditions so as to allow molecular weight discriminative interaction between the first polyion and the second polyion; and (d) employing a fluorescence polarization assay for determining an inhibiting effect of the agent on the induction of the molecular weight change of the first polyion.

According to yet another aspect of the present invention there is provided a method of testing an agent for its potential at inhibiting induction of degradation of a polyanion, the method comprising the steps of (a) subjecting the polyanion to degradation inducing conditions in a presence, in an absence or under several different concentrations of the agent; (b) interacting the polyanion with a polycation, the polycation being fluorescently labeled; (c) providing reaction conditions so as to allow molecular weight discriminative interaction between the polyanion and the polycation; and (d) employing a fluorescence polarization assay for determining an inhibiting effect of the agent on the induction of the molecular weight change of the polyanion.

According to still another aspect of the present invention there is provided a method of testing an agent for its potential at inhibiting induction of degradation of a polycation, the method comprising the steps of (a) subjecting the polycation to degradation inducing conditions in a presence, in an absence or under several different concentrations of the agent; (b) interacting the polycation with a polyanion, the polyanion being fluorescently labeled; (c) providing reaction conditions so as to allow molecular weight discriminative interaction between the polycation and the polyanion; and (d) employing a fluorescence polarization assay for determining an inhibiting effect of the agent on the induction of the molecular weight change of the polycation.

According to another aspect of the present invention there is provided a method of testing an agent for its potential at inhibiting induction of polymerization of a first polyion, the method comprising the steps of (a) subjecting the first polyion to polymerization inducing conditions in a presence, in an absence or under several different concentrations of the agent; (b) interacting the first polyion with a second polyion having an opposite charge, the second polyion being fluorescently labeled; (c) providing reaction conditions so as to allow molecular weight discriminative interaction between the first polyion and the second polyion; and (d) employing a fluorescence polarization assay for determining an inhibiting effect of the agent on the induction of the molecular weight change of the first polyion.

According to yet another aspect of the present invention there is provided a method of testing an agent for its potential at inhibiting induction of polymerization of a polyanion, the method comprising the steps of (a) subjecting the polyanion to polymerization inducing conditions in a presence, in an absence or under several different concentrations of the agent; (b) interacting the polyanion with a polycation, the polycation being fluorescently labeled; (c) providing reaction conditions so as to allow molecular weight discriminative interaction between the polyanion and the polycation; and (d) employing a fluorescence polarization assay for determining an inhibiting effect of the agent on the induction of the molecular weight change of the polyanion.

According to still another aspect of the present invention there is provided a method of testing an agent for its potential at inhibiting induction of polymerization of a polycation, the method comprising the steps of (a) subjecting the polycation to polymerization inducing conditions in a presence, in an absence or under several different concentrations of the agent; (b) interacting the polycation with a polyanion, the polyanion being fluorescently labeled; (c) providing reaction conditions so as to allow molecular weight discriminative interaction between the polycation and the polyanion; and (d) employing a fluorescence polarization assay for determining an inhibiting effect of the agent on the induction of the molecular weight change of the polycation.

According to another aspect of the present invention there is provided a method of testing an agent for its potential at activating induction of a molecular weight change of a first polyion, the method comprising the steps of (a) subjecting the first polyion to conditions under-which the first polyion undergoing the molecular weight change in a presence, in an absence or under several different concentrations of the agent; (b) interacting the first polyion with a second polyion having an opposite charge, the second polyion being fluorescently labeled; (c) providing reaction conditions so as to allow molecular weight discriminative interaction between the first polyion and the second polyion; and (d) employing a fluorescence polarization assay for determining an activating effect of the agent on the induction of the molecular weight change of the first polyion.

According to yet another aspect of the present invention there is provided a method of testing an agent for its potential at activating induction of a molecular weight change of a polyanion, the method comprising the steps of (a) subjecting the polyanion to conditions under-which the polyanion undergoing the molecular weight change in a presence, in an absence or under several different concentrations of the agent; (b) interacting the polyanion with a polycation, the polycation being fluorescently labeled; (c) providing reaction conditions so as to allow molecular weight discriminative interaction between the polyanion and the polycation; and (d) employing a fluorescence polarization assay for determining an activating effect of the agent on the induction of the molecular weight change of the polyanion.

According to still another aspect of the present invention there is provided a method of testing an agent for its potential at activating induction of a molecular weight change of a polycation, the method comprising the steps of (a) subjecting the polycation to conditions under-which the polycation undergoing the molecular weight change in a presence, in an absence or under several different concentrations of the agent; (b) interacting the polycation with a polyanion, the polyanion being fluorescently labeled; (c) providing reaction conditions so as to allow molecular weight discriminative interaction between the polycation and the polyanion; and (d) employing a fluorescence polarization assay for determining an activating effect of the agent on the induction of the molecular weight change of the polycation.

According to another aspect of the present invention there is provided a method of testing an agent for its potential at activating induction of degradation of a first polyion, the method comprising the steps of (a) subjecting the first polyion to degradation inducing conditions in a presence, in an absence or under several different concentrations of the agent; (b) interacting the first polyion with a second polyion having an opposite charge, the second polyion being fluorescently labeled; (c) providing reaction conditions so as to allow molecular weight discriminative interaction between the first polyion and the second polyion; and (d) employing a fluorescence polarization assay for determining an activating effect of the agent on the induction of the molecular weight change of the first polyion.

According to yet another aspect of the present invention there is provided a method of testing an agent for its potential at activating induction of degradation of a polyanion, the method comprising the steps of (a) subjecting the polyanion to degradation inducing conditions in a presence, in an absence or under several different concentrations of the agent; (b) interacting the polyanion with a polycation, the polycation being fluorescently labeled; (c) providing reaction conditions so as to allow molecular weight discriminative interaction between the polyanion and the polycation; and (d) employing a fluorescence polarization assay for determining an activating effect of the agent on the induction of the molecular weight change of the polyanion.

According to still another aspect of the present invention there is provided a method of testing an agent for its potential at activating induction of degradation of a polycation, the method comprising the steps of (a) subjecting the polycation to degradation inducing conditions in a presence, in an absence or under several different concentrations of the agent; (b) interacting the polycation with a polyanion, the polyanion being fluorescently labeled; (c) providing reaction conditions so as to allow molecular weight discriminative interaction between the polycation and the polyanion; and (d) employing a fluorescence polarization assay for determining an activating effect of the agent on the induction of the molecular weight change of the polycation.

According to another aspect of the present invention there is provided a method of testing an agent for its potential at activating induction of polymerization of a first polyion, the method comprising the steps of (a) subjecting the first polyion to polymerization inducing conditions in a presence, in an absence or under several different concentrations of the agent; (b) interacting the first polyion with a second polyion having an opposite charge, the second polyion being fluorescently labeled; (c) providing reaction conditions so as to allow molecular weight discriminative interaction between the first polyion and the second polyion; and (d) employing a fluorescence polarization assay for determining an activating effect of the agent on the induction of the molecular weight change of the first polyion.

According to yet another aspect of the present invention there is provided a method of testing an agent for its potential at activating induction of polymerization of a polyanion, the method comprising the steps of (a) subjecting the polyanion to polymerization inducing conditions in a presence, in an absence or under several different concentrations of the agent; (b) interacting the polyanion with a polycation, the polycation being fluorescently labeled; (c) providing reaction conditions so as to allow molecular weight discriminative interaction between the polyanion and the polycation; and (d) employing a fluorescence polarization assay for determining an activating effect of the agent on the induction of the molecular weight change of the polyanion.

According to still another aspect of the present invention there is provided a method of testing an agent for its potential at activating induction of polymerization of a polycation, the method comprising the steps of (a) subjecting the polycation to polymerization inducing conditions in a presence, in an absence or under several different concentrations of the agent; (b) interacting the polycation with a polyanion, the polyanion being fluorescently labeled; (c) providing reaction conditions so as to allow molecular weight discriminative interaction between the polycation and the polyanion; and (d) employing a fluorescence polarization assay for determining an activating effect of the agent on the induction of the molecular weight change of the polycation.

The present invention successfully addresses the shortcomings of the presently known configurations by providing a high throughput fluorescence polarization assay for monitoring degradation or polymerization of polyanions or polycations, which can be used to screen for modulators (inhibitors and activators) of these processes.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
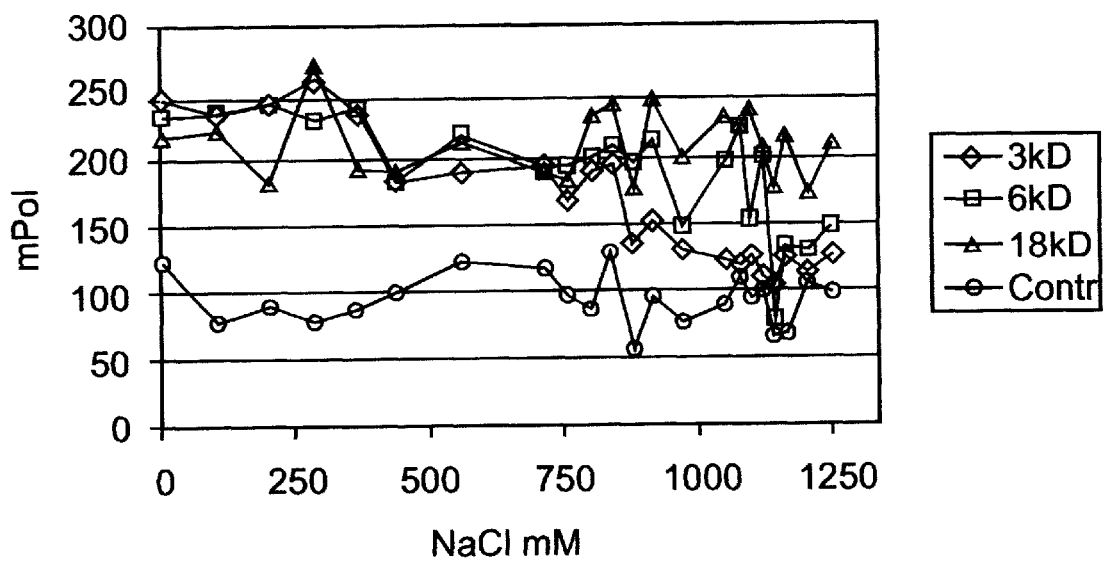
FIG. 1: Standard 100 $\mu$L reaction mixtures containing 17.5 $\mu$g of 3 kD, 6 kD, and 18 kD heparin or controls without heparin were analyzed with FITC labeled poly-lysine (PL) in the presence of the indicated salt concentrations. Fluorescence polarization (FP) was determined as described in the Examples section that follows.

The present invention is of a novel fluorescence polarization high throughput assay which can be used for monitoring polyion (polycation or polyanion) degradation or polymerization and to establish the molecular weight of a polyion of unknown molecular weight. Specifically, the present invention can be used to monitor the activity of enzymes which either degrade or polymerize polyions and to screen for potential modulators (inhibitors or activators) of such enzymes. Physical and chemical degradation/polymerization processes of polyions and modulators thereof can also be monitored by the method of the present invention. Still specifically, the present invention can be used for monitoring the catalytic activity of glycosaminoglycans (GAGs) degrading enzymes and to screen for modulators, especially inhibitors, thereof, thereby identifying potential anti-metastatic and anti-inflammatory agents.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Rational:

Fluorescence polarization can provide data on the degree of positional stability of molecules in solution. It is well known that there is a direct correlation between the size of a molecule and its positional stability. For large polymers, such as polyanions and polycations, positional stability translates into structural rigidity in solution. A fluorescently labeled polycation, such as poly-lysine, in solution, may acquire a free conformation characterized by low structural rigidity, however, if contacted with a polyanion, such as a nucleic acid, a conformational change is induced, helix structure is formed, and the structural rigidity, and therefore, the ability to maintain fluorescence polarization, increases. However, small as well as larger fragments of the polycation lead to the same result, i.e., they both stabilize the structure of the polycation to substantially the same degree, therefore, while fluorescence polarization can be used to determine the concentration of the polyanion, it cannot, per se, monitor a molecular weight change thereof, due to, for example, polymerization or degradation.

While conceiving the present invention, it was hypothesized that certain reaction conditions may be selected to discriminate between interaction of polycations and polyanions according to their size, thereby allowing the use of fluorescence polarization to monitor changes in molecular weight and/or to establish the molecular weight of polycations and polyanions of unknown molecular weight in a sample. For example, under conditions which will allow larger fragments of a polyanion to interact with a fluorescently labeled polycation of a given size, but will prevent interaction of smaller fragments of the polyanion from interacting with the fluorescently labeled polycation of the given size, fluorescent polarization should maximize as the polyanions fragments are larger and vice versa, allowing to monitor polymerization and/or degradation thereof and/or modulation (inhibition or activation) of these processes.

While reducing the present invention to practice, an assay that utilizes the ability of NaCl to induce dissociation between heparin (a polyanion) and poly-(L-lysine) (a polycation) was developed. It was experimentally found that different limiting concentrations of NaCl are required to dissociate poly-(L-lysine) and heparin of different molecular weights. This information was used to develop a potent high throughput fluorescence polarization assay that discriminates between heparin and heparin degradation products, which assay serves as an example of the many fluorescence polarization based assays provided by the present invention, as is further delineated hereinbelow, all of which are based on the ability of reaction conditions, such as ionic strength, pH, temperature and/or viscosity, to induce dissociation/association between interacting polyanions and polycations in a molecular weight dependent manner, thereby enabling the implementation of a fluorescence polarization assay.

Thus, according to the present invention there is provided a method of determining a molecular weight of a first polyion in a sample. The method is effected by implementing the following method steps: (a) the first polyion is interacted with a second polyion having an opposite charge, the second polyion being fluorescently labeled; (b) reaction conditions are provided so as to allow molecular weight discriminative interaction between the first polyion and the second polyion; and (c) a fluorescence polarization assay is employed for determining the molecular weight of the first polyion. As is further exemplified in the Examples section that follows, such a determination can be made using a calibration curve employing to this end samples of the first polyion of a known molecular weight. This basic method can be used, according to the teachings of the present invention, to monitor molecular weight changes of a variety of polyions, as described in the following.

Aspects of the invention:

Thus, according to one aspect of the present invention, there is provided a method of monitoring a molecular weight change of a first polyion. The method, according to this aspect of the present invention, is effected by implementing the following method steps: (a) the first polyion is subjected to conditions under-which the first polyion undergoes the molecular weight change; (b) the first polyion is interacted with a second polyion having an opposite charge, the second polyion being fluorescently labeled; (c) reaction conditions are provided so as to allow molecular weight discriminative interaction between the first polyion and the second polyion; and (d) a fluorescence polarization assay is employed for monitoring the molecular weight change of the first polyion.

According to another aspect of the present invention, there is provided a method of monitoring a molecular weight change of a polyanion. The method, according to this aspect of the present invention, is effected by implementing the following method steps: (a) the polyanion is subjected to conditions under-which the polyanion undergoes the molecular weight change; (b) the polyanion is interacted with a polycation, the polycation being fluorescently labeled; (c) reaction conditions are provided so as to allow molecular weight discriminative interaction between the polyanion and the polycation; and (d) a fluorescence polarization assay is employed for monitoring the molecular weight change of the polyanion.

According to still another aspect of the present invention, there is provided a method of monitoring a molecular weight change of a polycation. The method, according to this aspect of the present invention, is effected by implementing the following method steps: (a) the polycation is subjected to conditions under-which the polycation undergoes the molecular weight change; (b) the polycation is interacted with a polyanion, the polyanion being fluorescently labeled; (c) reaction conditions are provided so as to allow molecular weight discriminative interaction between the polycation and the polyanion; and (d) a fluorescence polarization assay is employed for monitoring the molecular weight change of the polycation.

According to yet still another aspect of the present invention, there is provided a method of monitoring degradation of a first polyion. The method, according to this aspect of the present invention, is effected by implementing the following method steps: (a) the first polyion is subjected to degradation inducing conditions; (b) the first polyion is interacted with a second polyion having an opposite charge, the second polyion being fluorescently labeled; (c) reaction conditions are provided so as to allow molecular weight discriminative interaction between the first polyion and the second polyion; and (d) a fluorescence polarization assay is employed for monitoring a molecular weight change of the first polyion.

According to yet another aspect of the present invention, there is provided a method of monitoring degradation of a polyanion. The method, according to this aspect of the present invention, is effected by implementing the following method steps: (a) the polyanion is subjected to degradation inducing conditions; (b) the polyanion is interacted with a polycation, the polycation being fluorescently labeled; (c) reaction conditions are provided so as to allow molecular weight discriminative interaction between the polyanion and the polycation; and (d) a fluorescence polarization assay is employed for monitoring a molecular weight change of the polyanion.

According to still another aspect of the present invention, there is provided a method of monitoring degradation of a polycation. The method, according to this aspect of the present invention, is effected by implementing the following method steps: (a) the polycation is subjected to degradation inducing conditions; (b) the polycation is interacted with a polyanion, the polyanion being fluorescently labeled; (c)

reaction conditions are provided so as to allow molecular weight discriminative interaction between the polycation and the polyanion; and (d) a fluorescence polarization assay is employed for monitoring a molecular weight change of the polycation.

According to yet another aspect of the present invention, there is provided a method of monitoring polymerization of a first polyion. The method, according to this aspect of the present invention, is effected by implementing the following method steps: (a) the first polyion is subjected to polymerization inducing conditions; (b) the first polyion is interacted with a second polyion having an opposite charge, the second polyion being fluorescently labeled; (c) reaction conditions are provided so as to allow molecular weight discriminative interaction between the first polyion and the second polyion; and (d) a fluorescence polarization assay is employed for monitoring a molecular weight change of the first polyion.

According to still another aspect of the present invention, there is provided a method of monitoring polymerization of a polyanion. The method, according to this aspect of the present invention, is effected by implementing the following method steps: (a) the polyanion is subjected to polymerization inducing conditions; (b) the polyanion is interacted with a polycation, the polycation being fluorescently labeled; (c) reaction conditions are provided so as to allow molecular weight discriminative interaction between the polyanion and the polycation; and (d) a fluorescence polarization assay is employed for monitoring a molecular weight change of the polyanion.

According to yet another aspect of the present invention, there is provided a method of monitoring polymerization of a polycation. The method, according to this aspect of the present invention, is effected by implementing the following method steps: (a) the polycation is subjected to polymerization inducing conditions; (b) the polycation is interacted with a polyanion, the polyanion being fluorescently labeled; (c) reaction conditions are provided so as to allow molecular weight discriminative interaction between the polycation and the polyanion; and (d) a fluorescence polarization assay is employed for monitoring a molecular weight change of the polycation.

According to still another aspect of the present invention, there is provided a method of testing an agent for its potential at modulating induction of a molecular weight change of a first polyion. The method, according to this aspect of the present invention, is effected by implementing the following method steps: (a) the first polyion is subjected to conditions under-which the first polyion undergoes the molecular weight change in a presence, in an absence or under several different concentrations of the agent; (b) the first polyion is interacted with a second polyion having an opposite charge, the second polyion being fluorescently labeled; (c) reaction conditions are provided so as to allow molecular weight discriminative interaction between the first polyion and the second polyion; and (d) a fluorescence polarization assay is employed for determining a modulating effect of the agent on the induction of the molecular weight change of the first polyion.

According to yet another aspect of the present invention, there is provided a method of testing an agent for its potential at modulating induction of a molecular weight change of a polyanion. The method, according to this aspect of the present invention, is effected by implementing the following method steps: (a) the polyanion is subjected to conditions under-which the polyanion undergoes the molecular weight change in a presence, in an absence or under several different concentrations of the agent; (b) the polyanion is interacted with a polycation, the polycation being fluorescently labeled; (c) reaction conditions are provided so as to allow molecular weight discriminative interaction between the polyanion and the polycation; and (d) a fluorescence polarization assay is employed for determining a modulating effect of the agent on the induction of the molecular weight change of the polyanion.

According to still another aspect of the present invention, there is provided a method of testing an agent for its potential at modulating induction of a molecular weight change of a polycation. The method, according to this aspect of the present invention, is effected by implementing the following method steps: (a) the polycation is subjected to conditions under-which the polycation undergoes the molecular weight change in a presence, in an absence or under several different concentrations of the agent; (b) the polycation is interacted with a polyanion, the polyanion being fluorescently labeled; (c) reaction conditions are provided so as to allow molecular weight discriminative interaction between the polycation and the polyanion; and (d) a fluorescence polarization assay is employed for determining a modulating effect of the agent on the induction of the molecular weight change of the polycation.

According to another aspect of the present invention, there is provided a method of testing an agent for its potential at modulating induction of degradation of a first polyion. The method, according to this aspect of the present invention, is effected by implementing the following method steps: (a) the first polyion is subjected to degradation inducing conditions in a presence, in an absence or under several different concentrations of the agent; (b) the first polyion is interacted with a second polyion having an opposite charge, the second polyion being fluorescently labeled; (c) reaction conditions are provided so as to allow molecular weight discriminative interaction between the first polyion and the second polyion; and (d) a fluorescence polarization assay is employed for determining a modulating effect of the agent on the induction of the molecular weight change of the first polyion.

According to yet another aspect of the present invention, there is provided a method of testing an agent for its potential at modulating induction of degradation of a polyanion. The method, according to this aspect of the present invention, is effected by implementing the following method steps: (a) the polyanion is subjected to degradation inducing conditions in a presence, in an absence or under several different concentrations of the agent; (b) the polyanion is interacted with a polycation, the polycation being fluorescently labeled; (c) reaction conditions are provided so as to allow molecular weight discriminative interaction between the polyanion and the polycation; and (d) a fluorescence polarization assay is employed for determining a modulating effect of the agent on the induction of the molecular weight change of the polyanion.

According to still another aspect of the present invention, there is provided a method of testing an agent for its potential at modulating induction of degradation of a polycation. The method, according to this aspect of the present invention, is effected by implementing the following method steps: (a) the polycation is subjected to degradation inducing conditions in a presence, in an absence or under several different concentrations of the agent; (b) the polycation is interacted with a polyanion, the polyanion being fluorescently labeled; (c) reaction conditions are provided so as to allow molecular weight discriminative interaction between the polycation and the polyanion; and (d) a fluorescence polarization assay is employed for determining a modulating effect of the agent on the induction of the molecular weight change of the polycation.

According to another aspect of the present invention, there is provided a method of testing an agent for its potential at modulating induction of polymerization of a first polyion. The method, according to this aspect of the present invention, is effected by implementing the following method steps: (a) the first polyion is subjected to polymerization inducing conditions in a presence, in an absence or under several different concentrations of the agent; (b) the first polyion is interacted with a second polyion having an opposite charge, the second polyion being fluorescently labeled; (c) reaction conditions are provided so as to allow molecular weight discriminative interaction between the first polyion and the second polyion; and (d) a fluorescence polarization assay is employed for determining a modulating effect of the agent on the induction of the molecular weight change of the first polyion.

According to yet another aspect of the present invention, there is provided a method of testing an agent for its potential at modulating induction of polymerization of a polyanion. The method, according to this aspect of the present invention, is effected by implementing the following method steps: (a) the polyanion is subjected to polymerization inducing conditions in a presence, in an absence or under several different concentrations of the agent; (b) the polyanion is interacted with a polycation, the polycation being fluorescently labeled; (c) reaction conditions are provided so as to allow molecular weight discriminative interaction between the polyanion and the polycation; and (d) a fluorescence polarization assay is employed for determining a modulating effect of the agent on the induction of the molecular weight change of the polyanion.

According to still another aspect of the present invention, there is provided a method of testing an agent for its potential at modulating induction of polymerization of a polycation. The method, according to this aspect of the present invention, is effected by implementing the following method steps: (a) the polycation is subjected to polymerization inducing conditions in a presence, in an absence or under several different concentrations of the agent; (b) the polycation is interacted with a polyanion, the polyanion being fluorescently labeled; (c) reaction conditions are provided so as to allow molecular weight discriminative interaction between the polycation and the polyanion; and (d) a fluorescence polarization assay is employed for determining a modulating effect of the agent on the induction of the molecular weight change of the polycation.

According to another aspect of the present invention, there is provided a method of testing an agent for its potential at inhibiting induction of a molecular weight change of a first polyion. The method, according to this aspect of the present invention, is effected by implementing the following method steps: (a) the first polyion is subjected to conditions under-which the first polyion undergoes the molecular weight change in a presence, in an absence or under several different concentrations of the agent; (b) the first polyion is interacted with a second polyion having an opposite charge, the second polyion being fluorescently labeled; (c) reaction conditions are provided so as to allow molecular weight discriminative interaction between the first polyion and the second polyion; and (d) a fluorescence polarization assay is employed for determining an inhibiting effect of the agent on the induction of the molecular weight change of the first polyion.

According to yet another aspect of the present invention, there is provided a method of testing an agent for its potential at inhibiting induction of a molecular weight change of a polyanion. The method, according to this aspect of the present invention, is effected by implementing the following method steps: (a) the polyanion is subjected to conditions under-which the polyanion undergoes the molecular weight change in a presence, in an absence or under several different concentrations of the agent; (b) the polyanion is interacted with a polycation, the polycation being fluorescently labeled; (c) reaction conditions are provided so as to allow molecular weight discriminative interaction between the polyanion and the polycation; and (d) a fluorescence polarization assay is employed for determining an inhibiting effect of the agent on the induction of the molecular weight change of the polyanion.

According to still another aspect of the present invention, there is provided a method of testing an agent for its potential at inhibiting induction of a molecular weight change of a polycation. The method, according to this aspect of the present invention, is effected by implementing the following method steps: (a) the polycation is subjected to conditions under-which the polycation undergoes the molecular weight change in a presence, in an absence or under several different concentrations of the agent; (b) the polycation is interacted with a polyanion, the polyanion being fluorescently labeled; (c) reaction conditions are provided so as to allow molecular weight discriminative interaction between the polycation and the polyanion; and (d) a fluorescence polarization assay is employed for determining an inhibiting effect of the agent on the induction of the molecular weight change of the polycation.

According to another aspect of the present invention, there is provided a method of testing an agent for its potential at inhibiting induction of degradation of a first polyion. The method, according to this aspect of the present invention, is effected by implementing the following method steps: (a) the first polyion is subjected to degradation inducing conditions in a presence, in an absence or under several different concentrations of the agent; (b) the first polyion is interacted with a second polyion having an opposite charge, the second polyion being fluorescently labeled; (c) reaction conditions are provided so as to allow molecular weight discriminative interaction between the first polyion and the second polyion; and (d) a fluorescence polarization assay is employed for determining an inhibiting effect of the agent on the induction of the molecular weight change of the first polyion.

According to yet another aspect of the present invention, there is provided a method of testing an agent for its potential at inhibiting induction of degradation of a polyanion. The method, according to this aspect of the present invention, is effected by implementing the following method steps: (a) the polyanion is subjected to degradation inducing conditions in a presence, in an absence or under several different concentrations of the agent; (b) the polyanion is interacted with a polycation, the polycation being fluorescently labeled; (c) reaction conditions are provided so as to allow molecular weight discriminative interaction between the polyanion and the polycation; and (d) a fluorescence polarization assay is employed for determining an inhibiting effect of the agent on the induction of the molecular weight change of the polyanion.

According to still another aspect of the present invention, there is provided a method of testing an agent for its potential at inhibiting induction of degradation of a polycation. The method, according to this aspect of the present invention, is effected by implementing the following method steps: (a) the polycation is subjected to degradation inducing conditions in a presence, in an absence or under several different concentrations of the agent; (b) the polycation is interacted with a polyanion, the polyanion being fluorescently labeled; (c) reaction conditions are provided so as to allow molecular weight discriminative interaction between the polycation and the polyanion; and (d) a fluorescence polarization assay is employed for determining an inhibiting effect of the agent on the induction of the molecular weight change of the polycation.

According to another aspect of the present invention, there is provided a method of testing an agent for its potential at inhibiting induction of polymerization of a first polyion. The method, according to this aspect of the present invention, is effected by implementing the following method steps: (a) the first polyion is subjected to polymerization inducing conditions in a presence, in an absence or under several different concentrations of the agent; (b) the first polyion is interacted with a second polyion having an opposite charge, the second polyion being fluorescently labeled; (c) reaction conditions are provided so as to allow molecular weight discriminative interaction between the first polyion and the second polyion; and (d) a fluorescence polarization assay is employed for determining an inhibiting effect of the agent on the induction of the molecular weight change of the first polyion.

According to yet another aspect of the present invention, there is provided a method of testing an agent for its potential at inhibiting induction of polymerization of a polyanion. The method, according to this aspect of the present invention, is effected by implementing the following method steps: (a) the polyanion is subjected to polymerization inducing conditions in a presence, in an absence or under several different concentrations of the agent; (b) the polyanion is interacted with a polycation, the polycation being fluorescently labeled; (c) reaction conditions are provided so as to allow molecular weight discriminative interaction between the polyanion and the polycation; and (d) a fluorescence polarization assay is employed for determining an inhibiting effect of the agent on the induction of the molecular weight change of the polyanion.

According to still another aspect of the present invention, there is provided a method of testing an agent for its potential at inhibiting induction of polymerization of a polycation. The method, according to this aspect of the present invention, is effected by implementing the following method steps: (a) the polycation is subjected to polymerization inducing conditions in a presence, in an absence or under several different concentrations of the agent; (b) the polycation is interacted with a polyanion, the polyanion being fluorescently labeled; (c) reaction conditions are provided so as to allow molecular weight discriminative interaction between the polycation and the polyanion; and (d) a fluorescence polarization assay is employed for determining an inhibiting effect of the agent on the induction of the molecular weight change of the polycation.

According to another aspect of the present invention, there is provided a method of testing an agent for its potential at activating induction of a molecular weight change of a first polyion. The method, according to this aspect of the present invention, is effected by implementing the following method steps: (a) the first polyion is subjected to conditions under-which the first polyion undergoes the molecular weight change in a presence, in an absence or under several different concentrations of the agent; (b) the first polyion is interacted with a second polyion having an opposite charge, the second polyion being fluorescently labeled; (c) reaction conditions are provided so as to allow molecular weight discriminative interaction between the first polyion and the second polyion; and (d) a fluorescence polarization assay is employed for determining an activating effect of the agent on the induction of the molecular weight change of the first polyion.

According to yet another aspect of the present invention, there is provided a method of testing an agent for its potential at activating induction of a molecular weight change of a polyanion. The method, according to this aspect of the present invention, is effected by implementing the following method steps: (a) the polyanion is subjected to conditions under-which the polyanion undergoes the molecular weight change in a presence, in an absence or under several different concentrations of the agent; (b) the polyanion is interacted with a polycation, the polycation being fluorescently labeled; (c) reaction conditions are provided so as to allow molecular weight discriminative interaction between the polyanion and the polycation; and (d) a fluorescence polarization assay is employed for determining an activating effect of the agent on the induction of the molecular weight change of the polyanion.

According to still another aspect of the present invention, there is provided a method of testing an agent for its potential at activating induction of a molecular weight change of a polycation. The method, according to this aspect of the present invention, is effected by implementing the following method steps: (a) the polycation is subjected to conditions under-which the polycation undergoes the molecular weight change in a presence, in an absence or under several different concentrations of the agent; (b) the polycation is interacted with a polyanion, the polyanion being fluorescently labeled; (c) reaction conditions are provided so as to allow molecular weight discriminative interaction between the polycation and the polyanion; and (d) a fluorescence polarization assay is employed for determining an activating effect of the agent on the induction of the molecular weight change of the polycation.

According to another aspect of the present invention, there is provided a method of testing an agent for its potential at activating induction of degradation of a first polyion. The method, according to this aspect of the present invention, is effected by implementing the following method steps: (a) the first polyion is subjected to degradation inducing conditions in a presence, in an absence or under several different concentrations of the agent; (b) the first polyion is interacted with a second polyion having an opposite charge, the second polyion being fluorescently labeled; (c) reaction conditions are provided so as to allow molecular weight discriminative interaction between the first polyion and the second polyion; and (d) a fluorescence polarization assay is employed for determining an activating effect of the agent on the induction of the molecular weight change of the first polyion.

According to yet another aspect of the present invention, there is provided a method of testing an agent for its potential at activating induction of degradation of a polyanion. The method, according to this aspect of the present invention, is effected by implementing the following method steps: (a) the polyanion is subjected to degradation inducing conditions in a presence, in an absence or under several different concentrations of the agent; (b) the polyanion is interacted with a polycation, the polycation being fluorescently labeled; (c) reaction conditions are provided so as to allow molecular weight discriminative interaction between the polyanion and the polycation; and (d) a fluorescence polarization assay is employed for determining an activating effect of the agent on the induction of the molecular weight change of the polyanion.

According to still another aspect of the present invention, there is provided a method of testing an agent for its potential at activating induction of degradation of a polycation. The method, according to this aspect of the present invention, is effected by implementing the following method steps: (a) the polycation is subjected to degradation inducing conditions in a presence, in an absence or under several different concentrations of the agent; (b) the polycation is interacted with a polyanion, the polyanion being fluorescently labeled; (c) reaction conditions are provided so as to allow molecular weight discriminative interaction between the polycation and the polyanion; and (d) a fluorescence polarization assay is employed for determining an activating effect of the agent on the induction of the molecular weight change of the polycation.

According to another aspect of the present invention, there is provided a method of testing an agent for its potential at activating induction of polymerization of a first polyion. The method, according to this aspect of the present invention, is effected by implementing the following method steps: (a) the first polyion is subjected to polymerization inducing conditions in a presence, in an absence or under several different concentrations of the agent; (b) the first polyion is interacted with a second polyion having an opposite charge, the second polyion being fluorescently labeled; (c) reaction conditions are provided so as to allow molecular weight discriminative interaction between the first polyion and the second polyion; and (d) a fluorescence polarization assay is employed for determining an activating effect of the agent on the induction of the molecular weight change of the first polyion.

According to yet another aspect of the present invention, there is provided a method of testing an agent for its potential at activating induction of polymerization of a polyanion. The method, according to this aspect of the present invention, is effected by implementing the following method steps: (a) the polyanion is subjected to polymerization inducing conditions in a presence, in an absence or under several different concentrations of the agent; (b) the polyanion is interacted with a polycation, the polycation being fluorescently labeled; (c) reaction conditions are provided so as to allow molecular weight discriminative interaction between the polyanion and the polycation; and (d) a fluorescence polarization assay is employed for determining an activating effect of the agent on the induction of the molecular weight change of the polyanion.

According to still another aspect of the present invention, there is provided a method of testing an agent for its potential at activating induction of polymerization of a polycation. The method, according to this aspect of the present invention, is effected by implementing the following method steps: (a) the polycation is subjected to polymerization inducing conditions in a presence, in an absence or under several different concentrations of the agent; (b) the polycation is interacted with a polyanion, the polyanion being fluorescently labeled; (c) reaction conditions are provided so as to allow molecular weight discriminative interaction between the polycation and the polyanion; and (d) a fluorescence polarization assay is employed for determining an activating effect of the agent on the induction of the molecular weight change of the polycation.

It will be appreciated that the reaction steps of each aspect of the invention need not be performed in the order listed, and may be co-performed in part or in whole.

Polyanions:

An anion is a negatively charged ion. A polyanion is a polymer characterized by a plurality of negative charges along its length. For some polyanions every single building block is negatively charged, whereas for other some of the building blocks are negatively charged. By negatively charged it is meant one or more negative charges. Examples of polyanions include, but are not limited to, proteoglicans, glycosaminoglycans, heparane sulfate, heparin and nucleic acids, such as RNA and DNA, poly glutamic acid (either poly-(L-glutamic acid), poly-(D-glutamic acid, or mixed L-glutamic acid and D-glutamic acid), poly aspartic acid (either poly-(L-aspartic acid), poly-(D-aspartic acid, or mixed L-aspartic acid and D-aspartic acid), and a mixed polymer including (L and/or D) glutamic acid and (L and/or D) aspartic acid residues.

Polyanion degradation:

Each of the above listed polyanions is degradable by physical, chemical and/or enzymatic means.

Physical degradation of polyanions can be effected by, for example, applying shear forces or sonication.

Enzymatic degradation of polyanions can be effected by specific enzymes. For example, proteoglicans, glycosaminoglycans, heparane sulfate and heparin are degraded by one or more of the following degrading enzymes heparanases, connective tissue activating peptide, heparinases, glucoronidases, heparitinases, hyluronidases, sulfatases and chondroitinases. Nucleic acids are degraded by various nucleases, either endo- or exo-nucleases, either DNases or RNases. Polypeptides are degraded by proteases.

Polyanion polymerization:

Each of the above listed polyanions is polymerizable by chemical and/or enzymatic means.

Chemical polymerization of polyanions can be effected by, for example, solid phase synthesis, which is well known and practiced for nucleic acids and polypeptides. Complex chemical reactions can be employed to synthesize other polyanions.

Enzymatic polymerization of polyanions can be effected by specific enzymes. For example, glycosyl transferases and sulfhydril transferases can be employed to synthesize proteoglicans, glycosaminoglycans, heparane sulfate and heparin. Nucleic acids are enzymatically synthesized using various DNA and RNA polymerases. Polypeptides can be synthesized in vitro using cell lysates in the presence of an appropriate RNA template.

Polycations:

A cation is a positively charged ion. A polycation is a polymer characterized by a plurality of positive charges along its length. For some polycations every single building block is positively charged, whereas for other, some of the building blocks are positively charged. By positively charged it is meant one or more positive charges. Examples of polycations include, but are not limited to, poly-lysine (either poly-(L-lysine), poly-(D-lysine, or mixed L-lysine and D-lysine), poly arginine (either poly-(L-arginine), poly-(D-arginine, or mixed L-arginine and D-arginine), a mixed polymer including (L and/or D) lysine and (L and/or D) arginine residues, spermine, spermidine, chitin and positively charged cellulose.

Polycation degradation:

Each of the above listed polycations is degradable by physical, chemical and/or enzymatic means.

Physical degradation of polycations can be effected by, for example, applying shear forces or sonication.

Enzymatic degradation of polycations can be effected by specific enzymes, such as a variety of proteases, chitinases and cellulases.

Polycation polymerization:

Each of the above listed polycations is polymerizable by chemical and/or enzymatic means.

Chemical polymerization of polycations can be effected by, for example, solid phase synthesis, which is well known and practiced for peptide synthesis. Complex chemical reactions can be employed to synthesize other polycations.

Enzymatic polymerization of polycations can be effected by specific enzymes. For example, peptides containing high representation of lysine/arginine can be synthesized in vitro using cell lysates in the presence of an appropriate RNA template. Chitin can be synthesized by chitin synthase and cellulose by cellulose synthase. Cellulose which is an uncharged polymer by nature can be positively charged by various, well know, chemical and enzymatic reactions.

Polyanion-polycation interactions:

Polyanions and polycations electrostatically interact therebetween due to the opposite charges they carry. This interaction depends to a large extent on reaction conditions, such as, but not limited to, the temperature, the ion strength, the pH and the viscosity.

pH change, for example, may alter the charge density of polyions. At low acidic pHs polyanions become protonated and neutralized, whereas polycations neutralize at high basic pHs. Experiments can be designed to select discriminative pHs for discriminating small polyions from larger polyions in their ability to interact with counterpart polyions of a given size. Such discriminative pHs may be acidic pHs so as to neutralize some of the charge of polyanions, or low pHs so as to neutralize some of the charge of polycations. Certain pH values can be experimentally determined so as to achieve effective discrimination for a given system of polyion degradation or polymerization. One of ordinary skills in the art would be able, based on the disclosure of the present invention, to devise an experimental system with which to determine optimal discriminative pH values, in a fashion similar to the optimization of salt concentration as is further detailed below. Doing so, one may use polyions of predetermined size and mixtures thereof for system calibration. Reaction pH can be determined using appropriate buffers, such as, but not limited to, Tris-HCl buffer, Citrate-phosphate buffer, Phosphate buffer, and Glycine-NaOH buffer.

Ionic strength may mask the charge density of polyions. Experiments can be designed to select discriminative ionic strength for discriminating small polyions from larger polyions in their ability to interact with counterpart polyions of a given size. Certain ionic strength values can be experimentally determined so as to achieve effective discrimination for a given system of polyion degradation or polymerization. One of ordinary skills in the art would be able, based on the disclosure of the present invention, to devise an experimental system with which to determine optimal discriminative ionic strength values, in a fashion similar to the optimization of NaCl concentration as is further detailed below. Doing so, one may use polyions of predetermined size and mixtures thereof for system calibration. Ionic strength can be altered in accordance to the present invention using any salt, including, but not limited to, halogen salts of monovalent cations (depicted in the first column of the periodic table, such as sodium, potassium, litium, etc.), divalent cations (of the second column of the periodic table, such as magnesium, calcium, etc.) or transition metals (e.g., manganese, ferrous, etc.), such as chloride salts, bromide salts, fluoride salts and iodide salts; sulfur or phosphorous salts of monovalent, divalent and transition metal cations, and any other salt that can mask ionic interaction. Organic salts such as, but not limited to, acetate salts, e.g., sodium acetate, magnesium acetate, etc. and ammonium salts, such as ammonium chloride, ammonium sulphate, etc. can also be employed. Salts can be used in any range of concentrations from several to several hundreds of mM and up to 1 M and more, depending on the salt used and the application.

Reaction temperature and viscosity are physical parameters which can be set to discriminate interactions between polyions based on their size. Again, one of ordinary skills in the art can devise a calibration protocol to select appropriate temperature and viscosity values so as to optimize discrimination.

The reaction conditions are preferably selected so as not to interfere with other steps of the assay. Thus, selected reaction conditions should allow the fluorophore to fluoresce and the enzyme (if employed) to exert its catalytic activity.

Fluorescent labeling of polyions:

Polyions can be fluorescently labeled using any one of a plurality of available protocols combined with any one of a plurality of available fluorophores.

For example, nucleic acids can be fluorescently tagged by a plurality of fluorophores which are covalently linked to nucleotides using template dependent synthesis. Such nucleotides are commercially available from, for example, Amersham Pharmacia Biotech, e.g., Cy5-dCTP (Cat. No. 27-2692-01) or Fluorescein dCTP, Cat. No. 27-2681-01.

Poly aspartic acid can be labeled with, for example, 5-(Bromomethyl)fluorescein (Molecular Probes, Cat. No. B-1355) according to the manufacturer instructions.

Modulation of degradation or polymerization:

Degradation and polymerization of polyions, be it enzymatic, chemical or physical degradation or polymerization, may be modulated by various factors. Enzyme activity modulators, including inhibitors and activators, provide an excellent example. Thus, the present invention can be used to screen for modulators of degradation and polymerization of polyions, especially those exerting their effect indirectly by interaction with enzymes executing such degradation or polymerization.

Fluorescence polarization assay for glycosidases, heparanase in particular:

In a presently preferred embodiment of the present invention the catalytic activity of glycosaminoglycan degrading enzymes in degrading glycosaminoglycans is tested. In particular, the catalytic activity of glycosaminoglycan degrading enzymes in degrading glycosaminoglycans in the presence of potential inhibitory agents is tested, so as to screen for potential glycosaminoglycan degrading enzyme inhibitors.

Thus, in one particular, the present invention provides a method of monitoring degradation of a glycosaminoglycan polyanion via a glycosaminoglycan degrading enzyme. The method is effected by implementing the following method steps, in which (a) the glycosaminoglycan polyanion is subjected to the glycosaminoglycan degrading enzyme; (b) the glycosaminoglycan polyanion is interacted with a polycation, the polycation is fluorescently labeled; (c) reaction conditions are provided so as to allow molecular weight discriminative interaction between the glycosaminoglycan polyanion and the polycation; and (d) a fluorescence polarization assay is employed for monitoring a molecular weight change of the polyanion.

In another particular, the present invention provides a method of testing an agent for its potential at inhibiting degradation of a glycosaminoglycan polyanion by a glycosaminoglycan degrading enzyme. The method is effected by implementing the following method steps, in which (a) the glycosaminoglycan polyanion is subjected to the glycosaminoglycan degrading enzyme in a presence, in an absence or under several different concentrations of the agent; (b) the glycosaminoglycan polyanion is interacted with a polycation, the polycation is fluorescently labeled; (c) reaction conditions are provided so as to allow molecular weight discriminative interaction between the glycosaminoglycan polyanion and the polycation; and (d) a fluorescence polarization assay is employed for determining an inhibiting effect of the agent on the degradation of the glycosaminoglycan polyanion by the glycosaminoglycan degrading enzyme.

As used herein in the specification and in the claims section below, the phrase "glycosidase catalytic activity" refers to an animal endoglycosidase hydrolyzing activity.

As used herein in the specification and in the claims section below, the phrase "glycosidase enzyme" refers to an enzyme having glycosidase catalytic activity. Examples include, but are not limited to, heparanase and types of glucoronidases, chondroitinase, hyaloronidase, neuraminidase, galactosidase, etc.

As used herein in the specification and in the claims section below, the phrase "heparanase catalytic activity" includes animal endoglycosidase hydrolyzing activity which is specific for heparin or heparan sulfate proteoglycan substrates, as opposed to the activity of bacterial enzymes (heparinase I, II and III) which degrade heparin or heparan sulfate by means of β-elimination.

As used herein in the specification and in the claims section below, the phrase "heparanase enzyme" refers to an enzyme having heparanase catalytic activity. Examples include human or any other natural mammalian heparanase which can be purified following the method described in U.S. Pat. No. 5,362,641 to Fuks, which is incorporated by reference as if fully set forth herein, or preferably recombinant mammalian heparanase, genes for which, and the expression and purification of which are described in length in U.S. patent application Ser. Nos. 08/922,170 now U.S. Pat. No. 5,968,822; 09/071,739 now U.S. Pat. No. 6,177,545; 09/071,618 now abandoned; 09/109,386 now abandoned; 09/258,892 now abandoned; and PCT applications US/17954, US99/09255 and US99/09256, all of which are incorporated herein by reference. It will be appreciated by one ordinarily skilled in the art, and it is demonstrated in the above patent documents, that using the human heparanase gene sequence one can readily clone, express and purify recombinant heparanase of any other mammal. This sequence of events, i.e., cloning a gene of one species based on the sequence of the same gene from another species, proved successful in hundreds of previous cases, especially since the polymerase chain reaction (PCR) is practiced therefor.

As used herein in the specification and in the claims section below, the phrase "recombinant enzyme" includes enzymes whose coding sequence have been or will be cloned and are expressed in an expression system. Recombinant heparanase includes heparanases treated for increased activity. Such treatment can include protease cleavage. It further includes modified heparanase sequences including, for example, an introduced protease cleavage site, which when cleaved provides enzyme activation. In particular it includes all the heparanase species described and discussed in U.S. patent application Ser. No. 09/260,038 now U.S. Pat. No. 6,348,344; and in PCT/US99/09256, which are incorporated by reference as if fully set forth herein. The expression system used to express recombinant heparanase according to the present invention may be any suitable expression system. Examples include, but are not limited to, insect cell expression systems, mammalian cell expression systems, and yeast cell expression systems, however, bacterial expression systems are not excluded, see U.S. patent application Ser. No. 09/071,618 now abandoned. Both crude or purified recombinant heparanase produced in, for example, bacteria, yeast, insect cells or mammalian cells, or any other expression system can be employed in context of the present invention.

As used herein the phrases "inhibiting heparanase catalytic activity" or "inhibiting glycosidase catalytic activity" refers an inhibition of the catalytic activity of the respective enzyme toward a specific substrate in a given assay. Thus, both (other) substrates and inhibitors qualify for inhibiting the catalytic activity of the respective enzymes.

The agent or agents screened for can be of any type.

One example include anti-heparanase antibodies. It is well known that by binding to the active site antibodies can be used to inhibit catalytic activity of an enzyme.

As used herein in the specification and in the claims section below, the term "antibody" refers to any monoclonal or polyclonal immunoglobulin, or a fragment of an immunoglobin such as sFv (single chain antigen binding protein), Fab1 or Fab2. The immunoglobulin could also be a "humanized" antibody, in which murine variable regions are fused to human constant regions, or in which murine complementarity-determining regions are grafted onto a human antibody structure (Wilder, R. B. et al., J. Clin. Oncol., 14:1383–1400, 1996). Unlike mouse or rabbit antibodies, "humanized" antibodies often do not undergo an undesirable reaction with the immune system of the subject. The terms "sFv" and "single chain antigen binding protein" refer to a type of a fragment of an immunoglobulin, an example of which is sFv CC49 (Larson, S. M. et al., Cancer, 80:2458–68, 1997).

Anti-heparanase antibodies are described in length in U.S. patent application Ser. No. 09/071,739 now U.S. Pat. No. 6,177,545 and in PCT/US99/09255, which are incorporated by reference as if fully set forth herein. Neutrelizing heparanase antibodies, as described, for example, in U.S. patent application Ser. No. 09/189,200 now U.S. Pat. No. 6,121,300, which is incorporated herein by reference, are of particular interest for their later use in inactivating heparanase catalytic activity.

Another examples include naturally or man-made (synthetic) agents. Candidate agents for inhibiting heparanase catalytic activity include, but are not limited to, polyanionic molecules, chemically modified species of heparin, size homogeneous oligosaccharides derived from depolymerized heparin, libraries of small molecules (combinatorial library of similar agents) and rationally designed molecules for anti-heparanase catalytic activity. Libraries of synthetic or natural agents are envisaged. Such libraries can be screened for potential heparanase inhibitors in accordance with the teachings of the present invention.

Applicability for high throughput (HTS) screening:

Several parameters define the fluorescence polarization assay described herein as highly suitable for HTS and suitable to robotics and automated equipment. This assay, as any other fluorescence polarization assay can be used in homogenous format without any separation or washing steps. It is very simple in the sense that it involves one or more steps of solvent addition(s) and reading. The assay is very sensitive as characterize by its ability to detect low levels of specific activity (FIG. 7).

The good signal to noise ratio, as well as reagent stability and insensitivity to DMSO in concentration ranging from 1 to 5%, show high level of assay robustness (FIG. 7). Finally, the assay can be miniaturized to 384 well plate format (40–50 µL/well) and also to 1536 well plate format (5–10 µL/well).

Scope of the invention:

The gist of the present invention relates to the use of reaction conditions discriminating between interaction of polycations and polyanions according to their size, thereby allowing the use of fluorescence polarization to monitor changes in, or to determine the molecular weight of polyions. One of skills in the art based on the disclosure provided herein would be able to practice the invention in a plurality of ways, including monitoring via fluorescence polarization, the degradation or polymerization of polycations or polyanions induced physically, chemically or enzymatically, in the presence, absence or different concentrations of modulators, including both inhibitors or activators, modulating the physical, chemical or enzymatic degradation or polymerization of polycations or polyanions. It will be appreciated that each assay devised calls for standardization, which standardization can be effected using the basic guidelines provided herein and exemplified below, combined with ordinary skills in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Experimental Methods

Labeling heparin with FITC: 9.3 mg poly-lysine (Sigma Cat. No. P2636) was incubated with 0.3 mg FITC (Sigma Cat. No. F7250) in the presence 0.5 mL of 0.5 M Sodium bicarbonate for 30 minutes at 47° C. The reaction product was purified on pre-equilibrated G-25 columns using 50 mM phosphate-citrate buffer, pH 5.4. Reaction products were collected in void volume and stored for future used.

Standard reaction: 100 µL containing 30 mM phosphate-citrate buffer, pH 5.4, 5 mM $CaCl_2$, and 63 mM NaCl (5×Hep buffer), 3.5 mM (FIGS. 3b, 4, 5) or 14 mM (FIG. 3a) heparin 18 kD (Sigma Cat. No. H3393), or markers of 6 kD or 3 kD (Sigma Cat. No. H2149 and H5027), 1% DMSO, and 0.12 units of purified heparanase (One units was defined as the activity of 300 ng purified enzyme) were incubated at 37° C. for three hours.

Poly-lysine Fluorescence polarization analysis: To 100 µL of reaction, a 100 µL mixture containing 5× Hep buffer, 1.6 M NaCl, 3.75 µg of poly-lysine, 0.5 µg of FITC labeled poly-lysine (fluorescence polarization mix) were added and mixed by pippetation. Samples were subjected to fluorescence polarization analysis using the PolarStar Galaxy (BMG, Germany) device. In early experiment (FIGS. 1, 2 and 3a) a 50 µL Fluorescence polarization mix containing 5×Hep buffer, 1.6 M NaCl, 3.75 µg of poly-lysine, 0.5 µg of FITC labeled poly-lysine and 2% triton X-100 were, mixed, incubated for 20 minutes at room temperature, then after, additional 50 µL 5×Hep buffer containing 1.6 M NaCl were added and following incubation of 20 minutes at room temperature samples were subjected to Fluorescence polarization analysis.

Experimental Results

The Fluorescence polarization assay exemplified herein is based on the ability of heparins and heparan sulfate (HS) to interact with poly-L-lysine and thus to induce alpha-helix conformation in FITC-labeled poly-lysine (Gelman R A, Blackwell J 1973. Heparin-polypeptide interactions in aqueous solution. *Arch. Biochem. Biophys.* 159(1):427–33). These conformational changes result in significant increase in the Fluorescence polarization value of poly-lysine, from ~100 to ~250 mP.

Discrimination between molecular sizes of heparins by Fluorescence polarization:

Heparanase degrades high molecular weight heparins into low molecular weight heparins. The data show that under normal assay conditions (low salt concentration), Fluorescence polarization analysis of poly-lysine interacting with heparin resulted with a relative high degree of polarization. Addition of equi-molar concentrations of sulfate units of 3 kD, 6 kD or 18 kD heparins resulted with similar high degree of polarization. However, gradual increase of salt (NaCl) concentration resulted in reduced Fluorescence polarization of poly-lysine, in a heparin molecular weight dependent manner (FIG. 1). Low molecular weight heparins (3 kD) showed reduced Fluorescence polarization in 800 mM NaCl and higher salt concentration were required to initiate reduction in Fluorescence polarization caused by heparins of higher molecular weight.

Figure 2:
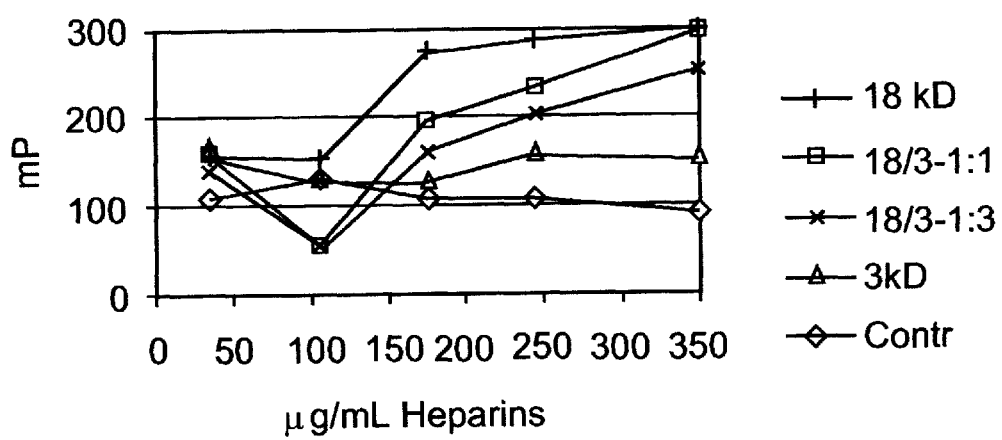
FIG. 2: Standard 100 $\mu$L reaction mixtures containing the indicated amounts 18 kD and 3 kD heparin and their mixes in 1:1 and 1:3 ratios (indicated as '18/3–1:3') or controls without heparin were analyzed with FITC labeled poly-lysine (PL) in the presence of 800 mM NaCl. Fluorescence polarization (FP) was determined as described in the Examples section that follows.

Using the Fluorescence polarization assay not only 3 kD was differentiated from 6 kD and 18 kD heparins but it was also applicable to identify mixes of different ratios of high and low molecular weight heparins. The effect of low molecular weight (3 kD), high molecular weight (18 kD) heparin and mixes of 3 kD and 18 kD heparin on the Fluorescence polarization of poly-lysine was tested. As shown in FIG. 2, highest and lowest Fluorescence polarization values were obtained when 18 kD and 3 kD heparin, respectively, were added to poly-lysine. Intermediates values of Fluorescence polarization were observed when mixes of 3 kD and 18 kD heparin were tested.

Two important conclusions may be drown from this experiment:

First, Fluorescence polarization values are strictly dependent on a critical minimal ratio of heparin to poly-lysine. 18 kD heparin at concentrations lower than this critical concentration can not induce an increase in the Fluorescence polarization of poly-lysine.

Second, high ratio of heparin/poly-lysine have little impact of Fluorescence polarization of homogenous population of either 3 kD or 18 kD heparins. By contrast, ratio of mixed populations of 3 and 18 kD heparins/poly-lysine determine the degree of Fluorescence polarization. The degree of Fluorescence polarization induced by mixed population of heparins under these conditions is dependent on the amount of 18 kD heparin in the mix. Maximal Fluorescence polarization is observed when the amount of 18 kD heparin in the mix is equal or higher than that required to induce maximal Fluorescence polarization by homogenous 18 kD heparin.

Figure 3A:
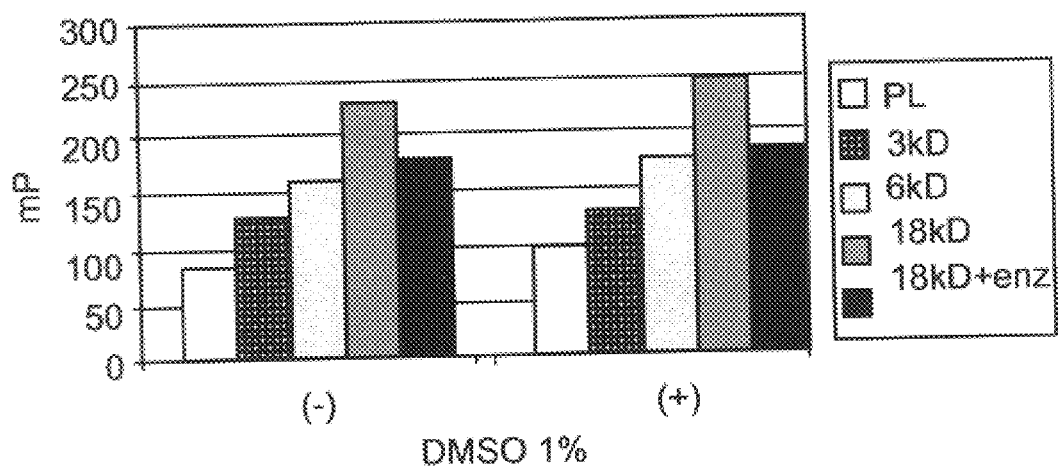
FIG. 3a: The following standard 100 $\mu$L reaction mixtures were tested in the absence or presence 1% DMSO: systems containing 25 $\mu$g of 18 kD heparin that were incubated with or without 0.12 units of heparanase for three hours and systems containing 3 kD, 6 kD, and 18 kD heparins or mixtures without heparin that were used as controls. Fluorescence polarization (FP) analysis following the addition of poly-lysine (PL) was performed as described in the Examples section that follows.
Figure 3B:
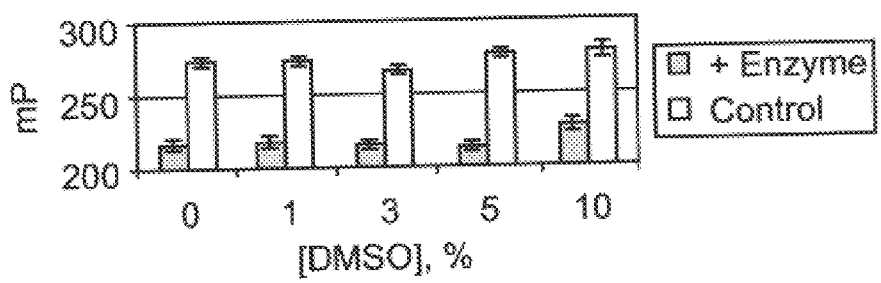
FIG. 3b: The following standard 100 $\mu$L reaction mixtures containing 6.5 $\mu$g of 18 kD heparin with (left column) or without (right column) 0.12 units of heparanase were incubated for two hours in the absence or presence of the indicated DMSO concentrations. Fluorescence polarization (FP) analysis following the addition of poly-lysine (PL) was performed as described in the Examples section that follows.

Since typically inhibitors are tested in the presence of 1% DMSO, the effect of addition of 1% DMSO on the Fluorescence polarization obtained by interaction of poly-lysine and each of the heparins was tested. Detection of enzyme activity as expressed by small versus large heparin fragments was possible up to 10% DMSO in the reaction mixture (FIG. 3b). In addition, it is also shown that heparanase activity and dynamic range is not affected by this treatment (FIGS. 3a and 3b).

Figure 4:
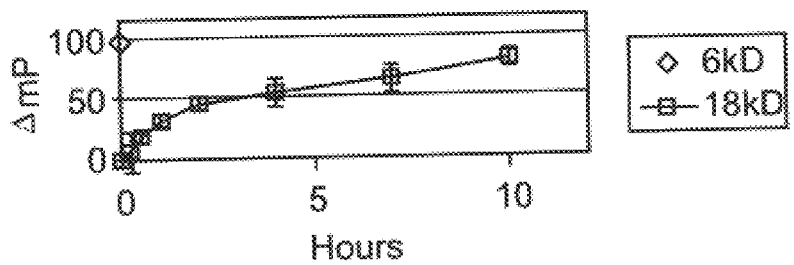
FIG. 4: The following standard reaction mixtures containing 6.5 $\mu$g of 18 kD heparin or 6 kD heparin were incubated for the indicated time with 0.12 units of heparanase. Fluorescence polarization (FP) analysis following the addition of poly-lysine (PL) was performed as described in the Examples section that follows.
Figure 5:
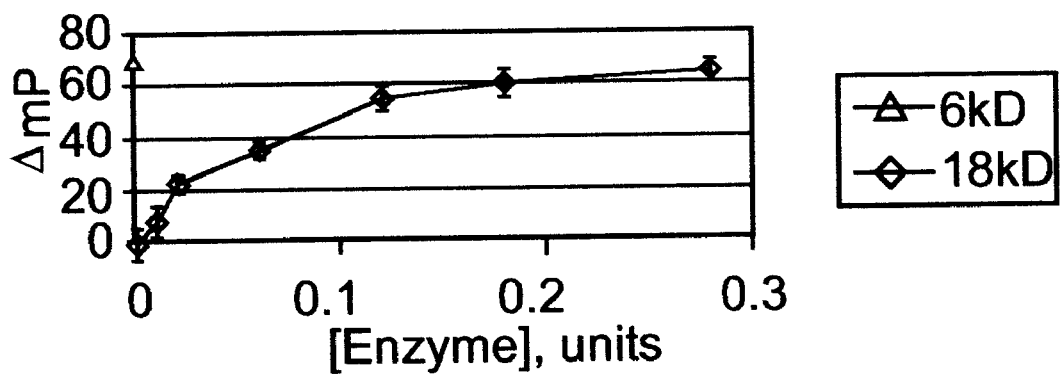
FIG. 5: The following standard reaction mixtures containing 6.5 $\mu$g of 18 kD heparin or 6 kD heparin marker were incubated with the indicated enzyme concentrations for two hours. Fluorescence polarization (FP) analysis following the addition of poly-lysine (PL) was performed as described in the Examples section that follows.
Figure 6:
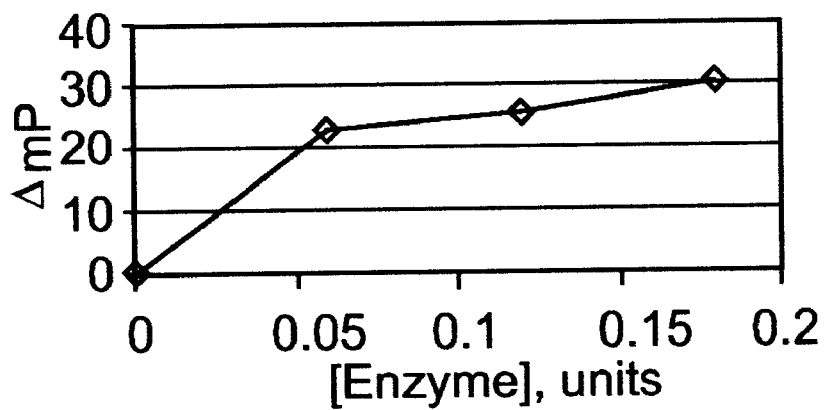
FIG. 6: The following reaction mixtures containing 6.5 $\mu$g of 40 kD heparan sulfate were incubated with the indicated enzyme concentrations for two hours. Fluorescence polarization (FP) analysis following the addition of poly-lysine (PL) was performed as described in the Examples section that follows.

Detection of heparanase enzymatic activity:

Using the Fluorescence polarization assay it was shown that heparanase activity is dependent on the reaction time (FIG. 4). The data demonstrates that heparanase activity is linear as a function of enzyme concentration when the reaction is carried out for as much as 2–3 hours. When the reaction is carried out for 6 hours, however, the reaction is closed to completion and therefore a typical saturation plot was observed. A typical dose response of enzymatic activity as a function of enzyme concentration was observed (FIG. 5). Similar results were obtained when the potential of the assay to determine hydrolysis of heparan sulfate by heparanase was tested (FIG. 6). Since heparin and heparan sulfate differ in their negative charge intensity and distribution, these results indicate the potential wide range of applications of the Fluorescence polarization assay described herein.

Inhibition of Fluorescence polarization activity by a heparanase inhibitor:

Using the fluorescence inhibition assay not only demonstrated enzymatic activity allows to monitor inhibition of heparanase catalytic activity by heparanase inhibitors. Being a fluorescence based assay, its ability to identify the potency of inhibitors is dependent on the fluorescence characterization of the inhibitors. Overlap in the absorbance and/or in the emission spectra of the tested compound and the fluorophore attached to poly-lysine may compromise the fidelity of the polarization value. This can be minimized by subtraction of background fluorescence intensity values.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of testing an agent for its potential at modulating induction of a molecular weight change of a first polymeric polyion, the method comprising the steps of:
    (a) subjecting the first polymeric polyion to conditions suitable for induction of molecular weight change in the first polyion at (i) a first concentration of the agent, and (ii) a second concentration of the agent, such that the agent may modulate the induction of the molecular weight change of the first polymeric polyion;
    (b) interacting the first polymeric polyion at the first concentration of the agent (i), with a second polymeric polyion having an opposite charge, such that the first polymeric polyion bonds to the second polymeric polyion primarily via ionic bonding to form a first complex, wherein the second polymeric polyion is fluorescently labelled;
    (c) interacting the first polymeric polyion at the second concentration of the agent (ii), with a second polymeric polyion having opposite charge. such that the first polymeric polyion bonds to the second polymeric polyion primarily via ionic bonding to form a second complex, wherein the second polymeric polyion is fluorescently labelled; and
    (d) determining a modulating effect of the agent on the induction of molecular weight change of the first polymeric polyion by measuring the fluorescence polarization of the first complex and the fluorescence polarization of the second complex and comparing the fluorescence polarization of the first and second complexes;
    wherein each of the first polymeric polyion and the second polymeric polyion have a plurality of either only positive charges or negative charges.

2. The method of claim 1, wherein the conditions are selected from the group consisting of a predetermined temperature, a predetermined ion strength, a predetermined pH and a predetermined viscosity.

3. The method of claim 1, wherein step (a) is performed in the presence of a plurality of concentrations of the agent.

4. The method of claim 1, wherein the conditions suitable for induction of molecular weight change in the first polymeric polyion are selected from the group consisting of degradation and polymerization.

5. The method of claim 4, wherein the conditions suitable for induction of molecular weight change in the first polymeric polyion are effected by degradation or polymerization induced by an enzyme or predefined physical conditions.

6. The method of claim 1, wherein the first polymeric polyion is selected from the group consisting of a polymeric polyanion and a polymeric polycation.

7. The method of claim 6, wherein the polymeric polyanion is selected from the group consisting proteoglycans, glycosaminoglycans, heparane sulfate, heparin, nucleic acids, poly-glutamic acid, poly aspartic acid, a mixed polymer including glutamic acid and aspartic acid residues.

8. The method of claim 6, wherein the polymeric polycation is selected from the group consisting of poly-lysine, poly arginine, a mixed polymer including lysine and arginine residues, spermine, spermidine, chitin and positively charged cellulose.

9. The method of claim 1, wherein the second polymeric polyion is selected from the group consisting of a polymeric polyanion and a polymeric polycation.

10. The method of claim 9, wherein the polymeric polyanion is selected from the group consisting proteoglycans, glycosaminoglycans, heparane sulfate, heparin, nucleic acids, poly-glutamic acid, poly aspartic acid, a mixed polymer including glutamic acid and aspartic acid residues.

11. The method of claim 9, wherein the polymeric polycation is selected from the group consisting of poly-lysine, poly arginine, a mixed polymer including lysine and arginine residues, spermine, spermidine, chitin and positively charged cellulose.

12. A method of testing an agent for its potential at modulating induction of a molecular weight change of a polymeric polyanion, said polymeric polyanion having a plurality of negative charges and is devoid of positive charges, the method comprising the steps of:
    (a) subjecting the polymeric polyanion to conditions suitable for induction of molecular weight change in the polymeric polyanion at (i) a first concentration of the agent, and (ii) a second concentration of the agent, such that the agent may modulate the induction of the molecular weight change of the polymeric polyanion;

(b) interacting the polymeric polyanion at the first concentration of the agent (i), with a polymeric polycation, such that the polymeric polyanion bonds to the polymeric polycation primarily via ionic bonding to form a first complex, wherein the polymeric polycation is fluorescently labelled;

(c) interacting the polymeric polyanion at the second concentration of the agent (ii), with a polymeric polycation, such that the first polymeric polyion bonds to the second polymeric polyion primarily via ionic bonding to form a second complex, wherein the polymeric polycation is fluorescently labelled; and (d) determining a modulating effect of the agent on the induction of molecular weight change of the polymeric polyanion by measuring the fluorescence polarization of the first complex and the fluorescence polarization of the second complex, and comparing the fluorescence polarization of the first and second complexes.

13. The method of claim 12, wherein the conditions are selected from the group consisting of a predetermined temperature, a predetermined ion strength, a predetermined pH and a predetermined viscosity.

14. The method of claim 12, wherein the agent is tested for its potential at modulating induction of a molecular weight change of a polymeric polyanion by heparanase.

15. The method of claim 12, wherein step (a) is performed in the presence of a plurality of concentrations of the agent.

16. The method of claim 12, wherein the conditions suitable for induction of molecular weight change in the polymeric polyanion are selected from the group consisting of degradation and polymerization.

17. The method of claim 16, wherein the conditions suitable for induction of molecular weight change in the polymeric polyanion are effected by degradation or polymerization induced by an enzyme or predefined physical conditions.

18. The method of claim 17, wherein the enzyme is a glycosaminoglycans degrading enzyme.

19. The method of claim 18, wherein the glycosaminoglycans degrading enzyme is selected from the group consisting of heparanases, connective tissue activating peptide, heparinases, glucoronidases, heparitinases, hyaluronidases, sulfates and chondroitinases.

20. The method of claim 18, wherein the glycosaminoglycans degrading enzyme is selected from the group consisting of a recombinantly produced enzyme and an enzyme purified from a natural source.

21. The method of claim 12, wherein the polymeric polyanion is selected from the group consisting proteoglycans, glycosaminoglycans, heparane sulfate, heparin, nucleic acids, poly-glutamic acid, poly aspartic acid, a mixed polymer including glutamic acid and aspartic acid residues.

22. The method of claim 21, wherein the polymeric polycation is selected from the group consisting of poly-lysine, poly arginine, a mixed polymer including lysine and arginine residues, spermine, spermidine, chitin and positively charged cellulose.

23. A method of testing an agent for its potential at inhibiting degradation of a glycosaminoglycan polyanion by a glycosaminoglycan degrading enzyme, said glycosaminoglycan polyanion having a plurality of negative charges and is devoid of positive charges, the method comprising the steps of:

(a) subjecting the glycosaminoglycan polyanion to the glycosaminoglycan degrading enzyme under conditions suitable for degrading the glycosaminoglycan polyanion at (i) a first concentration of the agent, and (ii) a second concentration of the agent, such that the agent may inhibit the degradation of the glycosaminoglycan polyanion;

(b) interacting the glycosaminoglycan polyanion at the first concentration of the agent (i), with a polymeric polycation, such that the glycosaminoglycan polyanion binds to the polymeric polycation primarily via ionic bonding to form a first complex, wherein the polymeric polycation is fluorescently labelled;

(c) interacting the glycosaminoglycan polyanion at the second concentration of the agent (ii), with a polymeric polycation, such that the glycosaminoglycan polyion binds to the polymeric polycation primarily via ionic bonding to form a second complex, wherein the polymeric polycation is fluorescently labelled; and (d) determining an inhibiting effect of the agent on the induction of molecular weight change of the glycosaminoglycan polyion by measuring the fluorescence polarization of the first complex and the fluorescence polarization of the second complex, and comparing the fluorescence polarization of the first and second complexes.

24. The method of claim 23, wherein step (a) is performed in the presence of a plurality of concentrations of the agent.

* * * * *